United States Patent
Blasberg et al.

(10) Patent No.: US 10,300,496 B2
(45) Date of Patent: May 28, 2019

(54) SILICON COMPRISING POLYMER COATED PARTICLES

(71) Applicants: BASF SE, Ludwigshafen (DE); BASF Corporation, Florham Park, NJ (US)

(72) Inventors: Florian Blasberg, Frankfurt (DE); Andreas Luz, Worms (DE); Igor Shishkov, Muenster (DE); David J. Gilbert, Ilvesheim (DE); Wolfgang Rohde, Speyer (DE)

(73) Assignees: BASF SE (DE); BASF Corporation, Florham Park, NJ (US)

( * ) Notice: Subject to any disclaimer, the term of this patent is extended or adjusted under 35 U.S.C. 154(b) by 85 days.

(21) Appl. No.: 15/112,788

(22) PCT Filed: Jan. 22, 2015

(86) PCT No.: PCT/EP2015/051292
§ 371 (c)(1),
(2) Date: Jul. 20, 2016

(87) PCT Pub. No.: WO2015/110555
PCT Pub. Date: Jul. 30, 2015

(65) Prior Publication Data
US 2016/0339446 A1  Nov. 24, 2016

(30) Foreign Application Priority Data
Jan. 22, 2014 (EP) .................................. 14152122

(51) Int. Cl.
*B01D 15/38* (2006.01)
*B03C 1/01* (2006.01)
(Continued)

(52) U.S. Cl.
CPC ............ *B03C 1/01* (2013.01); *B01D 15/3885* (2013.01); *B01J 20/10* (2013.01); *B01J 20/28009* (2013.01); *B01J 20/3204* (2013.01); *B01J 20/3272* (2013.01); *B01J 20/3293* (2013.01); *B22F 1/0018* (2013.01); *B22F 1/0062* (2013.01); *B22F 1/0096* (2013.01); *B22F 1/02* (2013.01); *C02F 1/288* (2013.01); *C02F 1/488* (2013.01); *C02F 1/5236* (2013.01); *C02F 1/545* (2013.01); *C02F 1/56* (2013.01); *C09C 1/24* (2013.01); *G01N 1/405* (2013.01); *H01F 1/0313* (2013.01); *H01F 1/33* (2013.01); *C01P 2004/51* (2013.01); *C01P 2004/61* (2013.01); *C01P 2004/62* (2013.01); *C01P 2004/64* (2013.01); *C01P 2006/12* (2013.01);
(Continued)

(58) Field of Classification Search
CPC ......... B32B 15/04; B32B 15/08; B32B 19/00; B32B 19/04; B32B 19/045; B32B 27/06; B32B 27/14; B32B 27/28; B32B 2255/04; B32B 2255/26; B32B 2264/105; B32B 2264/102; B32B 2307/73; C02F 1/5236; C02F 1/545; C02F 1/56; C02F 1/488; C02F 1/288; C02F 1/281; C02F 1/285; C02F 2305/04; B03C 1/01; H01F 1/0313; H01F 1/33; G01N 1/405; B22F 1/02; B22F 1/0018; B22F 1/0062; B22F 1/0096; B01D 15/3885; B01J 20/10; B01J 20/3204; B01J 20/3272; B01J 20/3293; B01J 20/28009; C09C 1/24; C09C 1/62; C09C 3/12; C01P 2004/51; C01P 2004/61; C01P 2004/62; C01P 2004/64; C01P 2006/12; C01P 2006/42
USPC ....... 210/638, 663, 679, 684, 688, 695, 702, 210/716, 729, 732, 774, 806; 428/403–405, 407, 692, 692.1, 689, 693, 428/693.1, 900
See application file for complete search history.

(56) References Cited

U.S. PATENT DOCUMENTS 2,375,998 A  5/1945  McGregor et al.
2,744,040 A  5/1956  Altmann
(Continued)

FOREIGN PATENT DOCUMENTS

EP  0989468 A2  3/2000
EP  1200408 A2  5/2002
(Continued)

OTHER PUBLICATIONS

International Search Report for PCT/EP2015/051292 dated Jun. 18, 2015.
(Continued)

*Primary Examiner* — Joseph W Drodge
(74) *Attorney, Agent, or Firm* — Drinker Biddle & Reath LLP

(57) ABSTRACT

The present invention relates to core-shell-particles, wherein the core comprises at least one metal, or a compound thereof, or a mixture of at least one metal or a compound thereof and at least one semimetal or a compound thereof, and the shell comprises at least one silicon comprising polymer, to a process for the preparation of these core-shell-particles, to the use of these core-shell-particles in an agglomeration-deagglomeration process, in particular in chemical, physical or biological test methods or separation processes, decontamination processes, water purification, recycling of electrical/electronic scrap or gravity separation, and to a process for separating at least one first material from a mixture comprising this at least one first material and at least one second material.

11 Claims, No Drawings

(51) Int. Cl.
*B01J 20/32* (2006.01)
*C02F 1/28* (2006.01)
*C02F 1/48* (2006.01)
*B01J 20/10* (2006.01)
*C02F 1/52* (2006.01)
*C02F 1/54* (2006.01)
*C02F 1/56* (2006.01)
*B22F 1/00* (2006.01)
*C09C 1/24* (2006.01)
*B01J 20/28* (2006.01)
*H01F 1/33* (2006.01)
*B22F 1/02* (2006.01)
*G01N 1/40* (2006.01)
*H01F 1/03* (2006.01)
*C09C 1/62* (2006.01)
*C09C 3/12* (2006.01)

(52) U.S. Cl.
CPC .......... *C01P 2006/42* (2013.01); *C02F 1/281* (2013.01); *C02F 1/285* (2013.01); *C02F 2305/04* (2013.01); *C09C 1/62* (2013.01); *C09C 3/12* (2013.01)

(56) References Cited

U.S. PATENT DOCUMENTS

| | | | | |
|---|---|---|---|---|
| 4,661,408 A * | 4/1987 | Lau | ............ | B03C 1/01 428/405 |
| 4,705,725 A * | 11/1987 | Glajch | ............ | C08J 7/12 210/656 |
| 4,834,898 A | 5/1989 | Hwang | | |
| 5,051,199 A | 9/1991 | Barwise | | |
| 5,073,272 A * | 12/1991 | O'Neill | ............ | C02F 1/5227 210/728 |
| 5,302,532 A * | 4/1994 | Lau | ............ | B01D 15/3809 210/656 |
| 5,736,349 A * | 4/1998 | Sasaki | ............ | B03C 1/01 435/7.94 |
| 7,566,500 B2 * | 7/2009 | Kohama | ............ | C08K 9/06 428/327 |
| 7,622,202 B2 * | 11/2009 | Maeda | ............ | B22F 1/02 428/405 |
| 9,387,485 B2 * | 7/2016 | Michailovski | ............ | B03C 1/01 |
| 2007/0189944 A1 * | 8/2007 | Kirkland | ............ | B01J 20/28004 423/118.1 |
| 2010/0028195 A1 | 2/2010 | Maeda et al. | | |
| 2013/0112605 A1 * | 5/2013 | Wyndham | ............ | B01J 20/283 210/198.3 |
| 2013/0193078 A1 * | 8/2013 | Soane | ............ | C02F 1/40 210/726 |
| 2014/0377166 A1 * | 12/2014 | Soane | ............ | C02F 1/54 423/580.1 |

FOREIGN PATENT DOCUMENTS

WO    WO-8301397 A1    4/1983
WO    WO-0109099 A2    2/2001
WO    WO-2009/059382 A1    5/2009

OTHER PUBLICATIONS

Skoog et al., "Principles of Instrumental Analysis", *International Student Edition*, 6th Edition, 28 pages (2007).
*Ullmann's Encyclopedia of Industrial Chemistry*, "Platinum Group Metals and Compounds", vol. 28, pp. 318-388 (2012).
Zisman, "Relation of the Quilibrium Contact Angle to Liquid and Solid Constitution", *American Chemical Society, U.S. Naval Research Laboratory, Advances in Chemistry Series*, pp. 1-57 (1964).

* cited by examiner

SILICON COMPRISING POLYMER COATED PARTICLES

CROSS-REFERENCE TO RELATED APPLICATIONS

This application is a national stage application (under 35 U.S.C. § 371) of PCT/EP2015/051292, filed Jan. 22, 2015, which claims benefit of European Application No. 14152122.9, filed Jan. 22, 2014, both of which are incorporated herein by reference in their entirety.

The present invention relates to core-shell-particles, wherein the core comprises at least one metal or a compound thereof, or a mixture of at least one metal or a compound thereof and at least one semimetal or a compound thereof, and the shell comprises at least one silicon comprising polymer; to a process for the preparation of these core-shell-particles; to the use of these core-shell-particles in an agglomeration-deagglomeration process, in particular in chemical, physical or biological test methods or separation processes, decontamination processes, water purification, recycling of electrical/electronic scrap or gravity separation; and to a process for separating at least one first material from a mixture comprising said at least one first material and at least one second material.

Metal oxide and/or semimetal oxide particles which are functionalized on the surface by means of silicon-comprising compounds are known from the prior art.

US 2010/0028195 A1 discloses a soft magnetic powder having a magnetic core and an insulating coating covering the surface of the core wherein the insulation coating contains silicon and 80% or more of silicon contained in the insulation coating constitutes a silsesquioxane skeleton, which compulsory contains functional groups like acrylic acid groups and cyclic ethers as polymer end groups.

WO 2009/059382 A1 discloses, for example, hydrophobic modification of mineral fillers and mixed polymer systems. According to this document, hydrophobic modification is effected by reaction of the corresponding mineral particles with silanes, for example $C_3$-$C_{12}$-alkyltrialkoxy silanes. That the correspondingly hydrophobically modified particles according to WO 2009/059382 A1 are particularly stable in large amounts of solvents, optionally in the presence of surface-active substances, is not disclosed in this document.

In the light of the prior art, it is thus an object of the present invention to provide particles which are hydrophobized on the surface and have a particularly high stability, in particular toward solvents and/or surface-active substances. It is a further object of the present invention to provide corresponding particles that can, for example, be used in processes in which these particles are in contact with solvents and/or surface-active substances, preferably in high amounts, and wherein high forces act onto the particles, wherein the hydrophobic surface shows improved stability under these conditions. A high stability of the hydrophobic surface should be advantageous since such particles may be reused, preferably without any work-up between the single cycles of a process. A further object of the present invention is to provide particles having a hydrophobic surface which is compatible with surface active substances that are used in the process.

These objects are achieved by core-shell-particles, wherein the core comprises at least one metal or a compound thereof, or a mixture of at least one metal or a compound thereof and at least one semimetal or a compound thereof, and the shell comprises at least one silicon comprising polymer comprising repeat units of the general formula (I)

$$—[SiR^1(OR^2)—O]—\quad (I)$$

wherein
R$^1$ is independently of another selected from hydrogen, linear or branched $C_1$-$C_{18}$-alkyl, unsubstituted or alkyl-substituted $C_5$-$C_{12}$-aryl, and
R$^2$ is independently of another selected from hydrogen, linear or branched $C_1$-$C_{18}$-alkyl, unsubstituted or alkyl-substituted $C_5$-$C_{12}$-aryl, or —SiR$^1_x$(OR$^2$)$_{3-x}$, wherein x is 1 or 2 and R$^1$ and R$^2$ have independently of another the meanings as mentioned above.

In one embodiment the present invention is directed to core-shell-particles, wherein the core comprises
(i) at least one metal or a compound thereof, or
(ii) a mixture of at least one metal or a compound thereof and at least one semimetal or a compound thereof,
and the shell comprises at least one silicon comprising polymer comprising repeat units of the general formula (I')

$$—[SiR^1—O_{1.5}]—\quad (I')$$

wherein
R$^1$ is independently of another selected from hydrogen, linear or branched $C_1$-$C_{18}$-alkyl, unsubstituted or alkyl-substituted $C_5$-$C_{12}$-aryl.

The present invention further relates to a process for the preparation of a core-shell-particle according to the present invention by coating the at least one core with at least one silicon comprising polymer comprising repeat units of the general formula (I) as mentioned above.

The present invention further relates to the use of a core-shell-particle according to the present invention in an agglomeration-deagglomeration process, in particular in chemical, physical or biological test methods or separation processes, decontamination processes, water purification, recycling of electrical/electronic scrap or gravity separation.

The present invention further relates to a process for separating at least one first material from a mixture comprising this at least one first material and at least one second material, which comprises the following steps:

(A) contacting of the mixture comprising at least one first material and at least one second material with at least one surface-modifying substance, optionally in the presence of at least one dispersant, resulting in the surface-active substance becoming attached to the at least one first material, (B) optionally, addition of at least one dispersant to the mixture obtained in step (A) to give a dispersion having a suitable concentration, (C) treatment of the dispersion from step (A) or (B) with at least one core-shell-particle according to the present invention, wherein the at least one metal, or a compound thereof, or a mixture of at least one metal or a compound thereof and at least one semimetal or a compound thereof is magnetic, so that the at least one first material to which the at least one surface-active substance is bound and the at least one core-shell-particle become attached to one another, (D) separation of the addition product from step (C) from the mixture by application of a magnetic field, (E) cleavage of the addition product which has been separated off in step (D) to obtain the at least one first material and the at least one core-shell-particle separately.

The present invention is further directed to a process for separating at least one first material from a mixture comprising said at least one first material and at least one second material, wherein the process comprises the following steps:

(A) contacting of the mixture comprising the at least one first material and the at least one second material with at least one surface-modifying substance, optionally in the presence of at least one dispersant, (B) optionally, addition of at least one dispersant to the mixture obtained in step (A), (C) treatment of the dispersion from step (A) or (B) with at least one core-shell-particle according to the present invention, wherein the at least one metal or a compound thereof, or a mixture of at least one metal or a compound thereof and at least one semimetal or a compound thereof is magnetic, and the at least one first material to which the at least one surface-modifying substance is attached and the at least one core-shell-particle form an agglomerate, and (D) separation of the agglomerate from step (C) from the mixture by application of a magnetic field.

Core-shell-particles according to the present invention have a core comprising at least one metal or a compound thereof, or a mixture of at least one metal or a compound thereof and at least one semimetal or a compound thereof.

In principle, the core-shell-particles according to the present invention may comprise any metal, or a compound thereof, or a mixture of any metal or a compound thereof and any semimetal or a compound thereof.

Preferred metals are selected from the group consisting of the metals of the main groups and transition metal groups of the Periodic Table of the Elements, in particular the transition metal groups of the Periodic Table of the Elements. As used herein, the term "transition metal group" includes lanthanides and actinides.

Examples of suitable metals of the main groups of the Periodic Table of the Elements are the alkali metals, for example Li, Na, K, Rb, or Cs; alkaline earth metals, for example Be, Mg, Ca, Ba, or Sr; the third main group of the Periodic Table of the Elements, for example Al, Ga, In, or Tl; the fourth main group of the Periodic Table of the Elements, for example Sn or Pb; or the fifth main group of the Periodic Table of the Elements, for example Sb or Bi.

Examples of suitable metals of the transition metal groups of the Periodic Table of the Elements are Sc, Y, the lanthanides, the actinides, Ti, Zr, Hf, Mn, Re, Fe, Ru, Os, Co, Rh, Ir, Ni, Pd, Pt, Cu, Ag, Au, Zn and Cd.

Preferred compounds of metals are selected from the group consisting of oxides, hydroxides, sulfides, (hydrogen) sulfates, (hydrogen)carbonates, (mono or dihydrogen)phosphates, halogenides, carbides, silicides and mixtures thereof.

Particularly preferred examples of metal oxides which are particularly suitable for the purposes of the invention are the oxides of the metals of the main groups and transition metal groups of the Periodic Table of the Elements, in particular the transition metal groups of the Periodic Table of the Elements.

In a preferred embodiment, the metal oxide used according to the invention is an oxide of the metals selected from the group consisting of Li, Na, K, Rb, Cs, Be, Mg, Ca, Ba, Sr, Al, Ga, In, Tl, Sn, Pb, Sb, Bi, Sc, Y, the lanthanides, the actinides, Ti, Zr, Hf, Mn, Re, Fe, Ru, Os, Co, Rh, Ir, Ni, Pd, Pt, Cu, Ag, Au, Zn, Cd and mixtures thereof. In one embodiment the metal oxide is preferably selected from the group consisting of Mn, Fe, Co, Ni, Cu and combinations thereof. Furthermore, mixed oxides of these metals, in particular Mn, Fe, Co, Ni or Cu, with at least one alkaline earth metal, for example Mg, Ca, Sr and/or Ba, are also suitable for the purposes of the invention.

The present invention therefore preferably provides a core-shell-particle, wherein the core comprises at least one metal compound, which is a metal oxide wherein the metal of the oxide is selected from the group consisting of Mn, Fe, Co, Ni, Cu, combinations thereof and mixed oxides of these metals with at least one alkaline earth metal, for example Mg, Ca, Sr and/or Ba.

According to a preferred embodiment of the present invention, the core-shell-particle comprises a magnetic core.

Particularly preferred magnetic materials are metal oxides like iron oxides, for example $Fe_2O_3$, magnetic iron oxides, for example magnetite, maghemite, hematite, cubic ferrites of the general formula (III)

$$M^{2+}{}_x Fe^{2+}{}_{1-x} Fe^{3+}{}_2 O_4 \qquad (III)$$

where

M is selected from among Co, Ni, Mn, Zn and mixtures thereof and x is ≤1, hexagonal ferrites, for example calcium, barium or strontium ferrite $MFe_6O_{19}$ where M=Ca, Sr, Ba, and combinations thereof.

In a preferred embodiment, the metal oxide used according to the invention is a magnetic iron oxide selected from the abovementioned group. In a very particularly preferred embodiment, the at least one metal oxide used according to the invention is magnetite. Magnetite has the formula $Fe_3O_4$, in particular $Fe^{II}Fe^{III}{}_2O_4$, and is known to those skilled in the art. Magnetite can be prepared by known processes, is commercially available and occurring in nature. Naturally occurring magnetite may further comprise magnesium, calcium, silica, potassium and/or sodium. Magnetite is commercially available, e.g. as magnetic pigment 345 (BASF SE) or magnetite from Höganäs.

The present invention therefore preferably relates to the core-shell-particle according to the present invention, wherein the at least one compound of at least one metal is selected from the group consisting of iron oxides, magnetic iron oxides and mixtures thereof. Magnetite is particularly preferred.

The metal oxide particles used according to the invention can optionally comprise dopants, for example further metals in oxidic or elemental form.

According to a further preferred embodiment of the core-shell-particle according to the present invention, the core comprises a mixture of at least one metal or a compound thereof and at least one semimetal or a compound thereof, particularly preferably an alloy, more preferred a magnetic alloy. A preferred semimetal is silicon. A preferred embodiment of the mixture comprising at least one metal or a compound thereof and at least one semimetal or a compound thereof is a magnetic iron-silicon-alloy.

The present invention therefore further preferably relates to core-shell-particle according to the present invention, wherein the core comprises a mixture of at least one metal or a compound thereof and at least one semimetal or a compound thereof, particularly preferably an alloy, more preferred a magnetic alloy, for example a magnetic iron-silicon-alloy.

According to a particularly preferred embodiment of the core-shell-particle according to the present invention the core is magnetic and comprises, preferably consists of, at least one material selected from the group of magnetic iron oxides, for example magnetite, maghemite, hematite, at least one alloy comprising a mixture of at least one metal and at least one semimetal, in particular a magnetic silicon-iron-alloy, and mixtures thereof.

According to a further preferred embodiment, the core of the core-shell-particle according to the present invention itself comprises a first coating of at least one inorganic material, for example selected from the group consisting of oxides of semimetals or metals, in particular metals of the transitions metal groups of the Periodic Table of the Elements. According to a preferred embodiment, the first coating comprises, in particular consists of, oxides of semimetals or metals selected from the group consisting of Zr, Al, Ti, Si and mixtures thereof.

According a preferred embodiment of this part of the present invention, the core comprises, in particular consists of, the materials that have been mentioned above, and the first coating comprises, in particular consist of, $ZrO_2$, $SiO_2$, $Al_2O_3$ and/or $TiO_2$. These cores comprising a first coating of at least one inorganic material further comprise a shell of the silicon comprising polymer as mentioned above to obtain the core-shell-particle according to the present invention.

The core-shell-particles according to the present invention comprise cores that in general may have any shape, for example for example spherical, cylindrical, acicular or cuboidal.

Further, the core-shell-particles according to the present invention comprise cores that in general may have a size, preferably a diameter, of about 50 nm to about 500 μm, preferably from about 200 nm to about 100 μm, particularly preferably from about 500 nm to about 50 μm, d90-values in each case. The definition of "d90" is known to the skilled artisan and means that 90% of the particles have a size that is lower than the value mentioned. These values can be acquired according to TEM (Transmission Electron Microscopy) or light diffraction methods, for example using a Malvern Mastersizer (such as a Mastersizer 2000 with software version 5.12G, wherein the sample is dispersed in an aqueous solution of $Na_4P2O7$).

The present invention therefore preferably relates to core-shell-particle according to the present invention, wherein the core has an average diameter of about 50 nm to about 500 μm, preferably from about 200 nm to about 100 μm, particularly preferably from about 500 nm to about 50 μm.

Further, the core-shell-particle according to the present invention comprises a shell having an average thickness of about 0.1 to about 1000 nm, preferably about 0.5 to about 200 nm, particularly preferably 0. about 5 to about 20 nm, even more preferred about 1 to about 20 nm. These values can be acquired according to TEM.

The present invention therefore preferably relates to core-shell-particles according to the present invention, wherein the shell has an average thickness of about 0.1 to about 1000 nm, preferably about 0.5 to about 200 nm, particularly preferably about 0.5 to about 20 nm, even more preferred about 1 to about 20 nm.

The core-shell-particles according to the present invention comprise a shell comprising at least one silicon comprising polymer comprising repeat units of the general formula (I)

—[SiR$^1$(OR$^2$)—O]—  (I)

wherein

R$^1$ is independently of another selected from hydrogen, linear or branched C$_1$-C$_{18}$-alkyl, unsubstituted or alkylsubstituted C$_5$-C$_{12}$-aryl, and R$^2$ is independently of another selected from hydrogen, linear or branched C$_1$-C$_{16}$-alkyl, unsubstituted or alkylsubstituted C$_5$-C$_{12}$-aryl, or —SiR$^1_x$(OR$^2$)$_{3-x}$, wherein x is 1 or 2 and R$^1$ and R$^2$ have independently of another the meanings as mentioned above.

According to the present invention, R$^1$ may be independently of another selected from hydrogen, linear or branched C$_1$-C$_{18}$-alkyl, unsubstituted or alkylsubstituted C$_5$-C$_{12}$-aryl.

In one preferred embodiment, R$^1$ is selected from linear or branched C$_8$-C$_{12}$-alkyl. Particularly preferred embodiments of R$^1$ concerning C$_8$-C$_{12}$-alkyl are n-octyl, n-nonyl, n-decyl, n-undecyl and n-duodecyl.

In another preferred embodiment. R$^1$ is selected from linear or branched C$_1$-C$_6$-alkyl. Particularly preferred embodiments of R$^1$ concerning C$_1$-C$_6$-alkyl are methyl, ethyl, propyl, like n- or isopropyl, butyl, like n-, iso- or tert.-butyl, pentyl, like n-, iso- or tert.-pentyl, hexyl, like n-, iso- or tert.-hexyl. In this embodiment, particularly preferably, R$^1$ is methyl.

Further preferred embodiments of R$^1$ concerning C$_5$-C$_{12}$-aryl are phenyl or naphthyl. Alkylsubstituents that may be present comprise 1 to 12 C-atoms and may be linear or branched. Preferred alkylsubstituted C5-C$_{12}$-aryls are toluyl, xylyl, benzyl, duryl. According to a preferred embodiment, R$^1$ is phenyl.

The present invention therefore preferably provides core-shell-particle according to the present invention, wherein R$^1$ in the general formula (I) is independently of another selected from the group consisting of methyl, n-ocytl, n-nonyl, n-decyl or phenyl.

Radicals R$^1$ as mentioned above are preferably not substituted by any functional group. The present invention therefore preferably relates to core-shell-particles according to the present invention, wherein R$^1$ in general formula (I) is not substituted by any functional group. According to the present invention, the wording "functional group" relates to chemically active groups like amino, amido, imido, hydroxy, ether, aldehyde, keto, carboxylic acid, thiol, thioether, hydroxamate or carbamate groups.

According to the present invention, R$^2$ may be independently of another selected from hydrogen, linear or branched C$_1$-C$_{18}$-alkyl, unsubstituted or alkylsubstituted C$_5$-C$_{12}$-aryl.

Preferably R$^2$ is selected from linear or branched C$_1$-C$_6$-alkyl. Particularly preferred embodiments of R$^2$ concerning C$_1$-C$_6$-alkyl are methyl, ethyl, propyl, like n- or iso-propyl, butyl, like n-, iso- or tert.-butyl, pentyl, like n-, iso- or tert.-pentyl, hexyl, like n-, iso- or tert.-hexyl. Particularly preferably, R$^1$ is methyl.

Further preferred embodiments of R$^2$ concerning C$_5$-C$_{12}$-aryl are phenyl or naphthyl. Alkylsubstituents that may be present comprises 1 to 12 C-atoms and may be linear or branched. Preferred alkylsubstituted C$_5$-C$_{12}$-aryls are toluyl, xylyl, benzyl, duryl.

Radicals R$^2$ as mentioned above are preferably not substituted by any functional group. The present invention therefore preferably relates core-shell-particles according to the present invention, wherein R$^2$ in general formula (I) is not substituted by any functional group. According to the present invention, the wording "functional group" relates to chemically active groups like amino, amido, imido, hydroxy, ether, aldehyde, keto, carboxylic acid, thiol, thioether, hydroxamate or carbamate groups.

According to the present invention R$^2$ may also be independently of another —SiR$^1_x$(OR$^2$)$_{3-x}$, wherein x is 1 or 2 and R$^1$ and R$^2$ have independently of another the meanings as mentioned above, wherein further radicals R$^2$ may also be —SiR$^1_x$(OR$^2$)$_{3-x}$. In case R$^2$ is ed —SiR$^1_x$(OR$^2$)$_{3-x}$; the R$^2$ group of this moiety may again be selected as —SiR$^1_x$(OR$^2$)$_{3-x}$, thus forming a chain or network of said groups within the silicone comprising polymer.

Parameter x in formula —SiR$^1_x$(OR$^2$)$_{3-x}$ describes the number of groups R$^1$ and OR$^2$ being present in this unit.

Parameter x may be 1 or 2, meaning that one or two group(s) $R^1$ are present resulting in two or one group(s) $OR^2$, respectively.

The silicon comprising polymer present in the shell of the core-shell-particles according to the present invention may further comprise repeat units of general formula (II)

wherein
$R^1$ is independently of another selected from hydrogen, linear or branched $C_1$-$C_{15}$-alkyl, unsubstituted or alkylsubstituted $C_5$-$C_{12}$-aryl.

The present invention therefore preferably relates to the core-shell-particle according to the present invention, wherein the silicon comprising polymer further comprises repeat units of general formula (II)

wherein
$R^1$ is independently of another selected from hydrogen, linear or branched $C_1$-$C_{18}$-alkyl, unsubstituted or alkylsubstituted $C_5$-$C_{12}$-aryl.

General and preferred embodiments of $R^1$ are mentioned above and apply independently of another accordingly to general formula (II).

According to a preferred embodiment of the present invention the silicon comprising polymer comprises more repeat units of general formula (I) and units —$SiR^1_x(OR^2)_{3-x}$ wherein x is 1 than repeat units of general formula (II) and units —$SiR^1_x(OR^2)_{3-x}$, wherein x is 2. Particularly preferably, the silicon comprising polymer according to the present invention comprises more than 90 mol-%, preferably more than 95 mol-%, repeat units of general formula (I) and units —$SiR^1_x(OR^2)_{3-x}$, wherein x is 1 and less than 10 mol-%, preferably less than 5 mol-%, repeat units of general formula (II) and units —$SiR^1_x(OR^2)_{3-x}$, wherein x is 2.

According to the preferred embodiment of the present invention branched silicon comprising polymers are present in the shell.

Therefore, the present invention preferably relates to core-shell-particles according to the present invention, wherein the silicon comprising polymer is branched.

According to the present invention, the number of repeat units that is present in the silicon comprising polymer is the sum of the number of repeat units according to general formula (I), (II), if present, and the number of groups $R^2$ having the meaning —$SiR^1_x(OR^2)_{3-x}$, if present.

According to a preferred embodiment of the core-shell-particle according to the present invention, the sum of the number of repeat units according to general formula (I), of repeat units according to general formula (II), if present, and the number of groups $R^2$ having the ing —$SiR^1_x(OR^2)_{3-x}$, is 10 to about 100000, more preferred 10 to about 10000, particularly preferred 10 to about 1000, for example about 50 to about 500, more preferably about 80 to about 120. The number of repeat units can be acquired via the molecular weight Mw of the silicon comprising polymer.

The present invention therefore preferably relates to the core-shell-particles according to the present invention, wherein the sum of the number of repeat units according to general formula (I), of repeat units according to general formula (II), if present, and the number of groups $R^2$ having the meaning —$SiR^1_x(OR^2)_{3-x}$, if present, is 10 to about 100000, more preferred 10 to about 10000, particularly preferred 10 to about 1000, for example about 50 to about 500, more preferably about 80 to about 120.

According to a further preferred embodiment of the core-shell-particles according to the present invention the silicon comprising polymer has a molecular weight Mw of about 500 to about 500000 g/mol, preferably about 1000 to about 250000 g/mol, more preferably about 3000 to about 50000 g/mol, for example about 5000 to about 10000 g/mol, weight average value in each case. The molecular weight Mw of the silicon comprising polymer according to the present invention can be acquired using Gel Permeation Chromatography (GPC) and/or Size Exclusion Chromatography (SEC). Both methods are known to the skilled artisan and are, for example, described in Skoog, D. A., Principles of Instrumental Analysis, 6$^{th}$ ed., Thompson Brooks/Cole: Belmont, Calif., 2006.

The present invention therefore preferably relates to the core-shell-particles according to the present invention, wherein the silicon comprising polymer has a molecular weight Mw of about 500 to about 500000 g/mol, preferably about 1000 to about 250000 g/mol, more preferably about 3000 to about 50000 g/mol, for example about 5000 to about 10000 g/mol, weight average value in each case.

According to a preferred embodiment of the core-shell-particles according to the present invention the silicon comprising polymer is terminated with groups $R^1$ as defined above and/or groups —$OR^2$, wherein $R^2$ is independently of another hydrogen, linear or branched $C_1$-$C_{18}$-alkyl or unsubstituted or alkylsubstituted $C_5$-$C_{12}$-aryl. Particularly preferred terminating groups of the silicon comprising polymer according to the present invention are methyl, n-octyl, n-nonyl, n-decyl and/or phenyl in respect of $R^1$.

The present invention therefore preferably relates to core-shell-particles according to the present invention, wherein the silicon comprising polymer is terminated with groups $R^1$ as defined above and/or groups —$OR^2$, wherein $R^2$ is independently of another hydrogen, linear or branched $C_1$-$C_{18}$-alkyl or unsubstituted or alkylsubstituted $C_5$-$C_{12}$-aryl.

According to one embodiment of the present invention the silicon comprising polymers do preferably not chemically react with the surface of the at least one core that is to be coated, but the at least one silicon comprising polymer is present on the surface as a physical coating.

In one embodiment, the shell of the core-shell-particle does not comprise a metal-based curing agent, wherein the metal based curing agent is represented by formula $(RO)_z$Met, wherein R is a $C_1$-$C_{16}$ alkyl group, Met is selected from the group consisting of Al, Ti, Na, K, Ca, Zn, and Fe and z is an integer of 1 to 4, In another embodiment of the present invention the shell of the core-shell-particle does not comprise a metal-based curing agent.

In one embodiment of the present invention, the shell of the core-shell particle does not comprise a silane-based coupling agent or a silane-based coupling agent oligomer.

The present invention further relates to a process for the preparation of a core-shell-particle according to the present invention by coating the at least one core with at least one silicon comprising polymer according to general formula (I) as defined above.

The process of the invention can, for example, be carried out by spraying a reagent solution comprising the silicon comprising polymer of the general formula (I) onto the at least one core. A further method of bringing the cores to be coated and a silicon comprising polymer of the general formula (I) as defined above into contact with one another comprises, for example, suspending the cores in a silicon comprising polymer of the general formula (I) or in a solution of a silicon comprising polymer of the general formula (I) in a suitable solvent. Corresponding processes are known per se to those skilled in the art.

The coating of the abovementioned silicon comprising polymer according to general formula (I) onto the at least one core can be carried out by processes known to those skilled in the art, for example by contacting of the substrates in a solvent, for example aromatic solvents like toluene, o-xylene, m-xylene, p-xylene; and/or other organic solvents selected from the group consisting of alcohols like ethanol, n-butanol, i-butanol; ketones like acetone; hydrocarbons like octane, nonane, decane, and mixtures thereof, at a temperature in the range from room temperature to the boiling point of the solvent. Afterwards, the slurry comprising the at least one core, the at least one silicon comprising polymer and the solvent is stirred. Under reduced pressure, for example at less than 1 bar, for example less than 800 mbar, further preferred less than 500 mbar, the solvent is removed and the silicon comprising polymer is coated onto the cores. After conventional work-up, the coating product of the at least one core and the silicon comprising polymer can be obtained. According to one embodiment of the present invention the coated particles can be heat treated, for example in a conventional oven that is known to the skilled artisan, at a temperature of 180 to 220° C., typically for 0.5 to 2 hours.

The present invention further relates to the use of a core-shell-particle according to the present invention in an agglomeration-deagglomeration process, in particular in chemical, physical or biological test methods or separation processes, decontamination processes, water purification, recycling of electrical/electronic scrap or gravity separation.

According to the invention, an agglomeration-deagglomeration cycle is a process in which the core-shell-particles of the invention, in particular magnetic core-shell-particles, are brought into contact with themselves or other particles, substances, materials, etc., in solution or dispersion and agglomerate as a result of hydrophobic interaction, ionic forces, van der Waals interactions and/or other attractive forces. These agglomerates are then processed in further processes, for example separated from other components and/or the solution or dispersion. After this treatment, the agglomerates may then be separated again, i.e. deagglomerated, so that the core-shell-particles and the other particles, substances, materials, etc., are again present separately (deagglomeration).

Examples of agglomeration-deagglomeration cycles which are preferred according to the invention are chemical, physical or biological test methods or separation processes, decontamination of contaminated, for example heavy metal-contaminated earth, water purification, recycling of electrical/electronic scrap or gravity separation.

The core-shell-particles according to the present invention are preferably used in a separation process for the separation of value containing matter containing material from ore material or from slag material, wherein the value containing matter containing material(s) are agglomerated with magnetic core-shell-particles according to the present invention, the magnetic agglomerates are then magnetically separated, and afterwards the agglomerates are disaggregated to obtain the value containing matter containing material in a more concentrated form.

In chemical, physical or biological test methods or separation processes, use is made of, for example, specifically modified magnetic core-shell-particles which e.g. have anchor groups for a specific antigen or virus, e.g. borrelia, HIV, hepatitis, on their surface. Bonding of these antigens/viruses to the core-shell-particles (agglomeration) enables these constituents to be separated off from a solution by means of magnetic separation and thus detected. The core-shell-particles are then recycled by means of surfactants which again release the electrostatic, adhesive or van der Weals interaction between core-shell-particles and antigen/virus (deagglomeration). In this way, the core-shell-particles can be reused.

The core-shell-particles of the invention, in particular magnetic core-shell-particles, can be used in water purification. Here, for example, it is possible to use core-shell-particles particles which remove organic constituents, suspended materials or fat droplets from the water by effecting hydrophobic agglomeration between the core-shell-particles and the hydrophobic contaminant. These hydrophobic agglomerates can be separated off by magnetic separation. In order for the water purification to be economical, it is useful to "unload" the core-shell-particles from the contaminant again and return them to the circuit. This "unloading" can once again be affected by deagglomeration using a specific surface-active substance (a surfactant), in particular a non-ionic surfactant, and/or by means of a specific solvent or solvent mixture.

Recycling of electrical/electronic scrap can, for example, be carried out by magnetic recovery of materials of value (Ir, Pt, Ru) from electrical/electronic scrap, once again preferably using core-shell-particles which, after hydrophobicization of the materials of value to be separated, can agglomerate with these and be separated off. After the agglomerates have been separated off, they are optionally deagglomerated again so that the core-shell-particles can be reused, or processed further via e.g. smelting without deagglomeration and core-shell-particles recycling step.

A further example is gravity separation, e.g. by means of cyclones known to those skilled in the art. In this way, relatively dense constituents can be separated off from less dense constituents by means of a gravity separation. If the densities of the individual components differ only slightly, e.g. Pt-doped hematite and undoped hematite, the density of the component to be separated off can be increased by agglomeration with a further component. Here, for example, the Pt-doped hematite component is coated according to the invention to give core-shell-particles, so that addition of hydrophobicized barium sulfate gives an agglomerate of the modified hematite and barium sulfate which has a greater density difference from the undoped hematite. After the agglomerate has been separated off, it can be deagglomerated again.

An advantage of the invention is that the core-shell-particles according to the invention are stable under the conditions prevailing in agglomeration and especially deagglomeration and can therefore preferably be reused. The reuse of the core-shell-particles of the invention allows for processes requiring less raw material(s) and thus the process can be performed more cost efficient.

In one embodiment, the present invention further relates to a process for separating at least one first material from a mixture comprising this at least one first material and at least one second material, which comprises the following steps:

(A) contacting of the mixture comprising at least one first material and at least one second material with at least one surface-modifying substance, optionally in the presence of at least one dispersant, resulting in the surface-modifying substance becoming attached to the at least one first material, (B) optionally, addition of at least one dispersant to the mixture obtained in step (A) to give a dispersion having a suitable concentration, (C) treatment of the dispersion from step (A) or (B) with at least one core-shell-particle according to the present invention, wherein the at least one metal, or a compound thereof, or a mixture of at least one metal or a compound thereof and at least one semimetal or a compound thereof is magnetic, so that the at least one first material to which the at least one surface-modifying substance is bound and the at least one core-shell-particle agglomerate to obtain an addition product, (D) separation of the addition product from step (C) from the mixture by application of a magnetic field, (E) cleavage of the addition product which has been separated off in step (D) to obtain the at least one first material and the at least one core-shell-particle separately.

In another embodiment the present invention is directed to a process for separating at least one first material from a mixture comprising said at least one first material and at least one second material, wherein the process comprises the following steps:

(A) contacting of the mixture comprising the at least one first material and the at least one second material with at least one surface-modifying substance, optionally in the presence of at least one dispersant, (B) optionally, addition of at least one dispersant to the mixture obtained in step (A), (C) treatment of the dispersion from step (A) or (B) with at least one core-shell-particle according to the present invention, wherein the at least one metal or a compound thereof, or a mixture of at least one metal or a compound thereof and at least one semimetal or a compound thereof is magnetic, and the at least one first material to which the at least one surface-modifying substance is attached and the at least one core-shell-particle form an agglomerate, and (D) separation of the agglomerate from step (C) from the mixture by application of a magnetic field.

The single steps of the process according to the present invention are explained in more detail in the following:

Step (A);

Step (A) of the process of the invention comprises contacting a mixture comprising at least one first material and at least second material with at least one surface-modifying substance, optionally in the presence of at least one dispersant.

By such contact, the surface-modifying substance attaches to the at least one first material.

The process of the invention is preferably employed for separating at least one first, hydrophobic material from a mixture comprising this at least one first, hydrophobic material and at least one second, hydrophilic material.

Dispersion media for dispersion as per step (A) of the process of the invention are selected from the group consisting of water, water-soluble organic compounds, such as alcohols (e.g. $C_1$-$C_6$ alcohols) and mixtures thereof, particularly preferably water.

In a preferred embodiment of the process of the invention, the at least one first material is at least one hydrophobic metal compound and the at least one second material is preferably at least one hydrophilic metal compound.

Thus, the at least one first material to be separated off is preferably a metal compound selected from the group consisting of sufidic ores, oxidic and/or carbonate-comprising ores, for example azurite $[Cu_3(CO_3)_2(OH)_2]$ or malachite $[Cu_2[(OH)_2|CO_3]]$, and the noble metals and their compounds to which a surface-active compound can become selectively attached to produce hydrophobic surface properties.

Examples of the at least one first material, being preferably the hydrophobic or hydrophobizable metal compound to be separated off are preferably sulfidic compounds selected from the group consisting of sulfidic ores, oxidic and/or carbonate-comprising ores, for example azurite $[Cu_3(CO_3)_2(OH)_2]$ or malachite $[Cu_2[(OH)_2|CO_3]]$, rare earth metals comprising ores like bastnaesite (Y, Ce, La)$CO_3$F, monazite (RE)$PO_4$ (RE=rare earth metal) or chrysocolla $(Cu,Al)_2H_2Si_2O_5(OH)_4$ hydrate, noble metals in elemental form and their compounds to which a surface modifying compound can become selectively attached to produce hydrophobic properties. Examples of noble metals that may be present as at least one first material are Au, Pt, Pd, Rh etc., preferably in the native state or as sulphides, phosphides, selenides, tellurides or as alloys with bismuth, antimony and/or other metals. Further examples of sulfidic ores that can be separated off according o the present invention are, for example, selected from the group of copper ores consisting of covellite CuS, molybdenum(IV) sulfide, chalcopyrite (cupiferous pyrite) $CuFeS_2$, bornite $Cu_5FeS_4$, chalcocite (copper glass) $Cu_2S$, pendlandite $(Fe,Ni)_9S_8$ and mixtures thereof.

Further examples of platinum group metal sulfides include vysotskite, braggite, cooperite or their solid solution in other sulfide minerals like pentlandite or base metal sulfides like chalcopyrite. Further none-sulfide separable Platinum-Group-Metals (PGM) minerals may be hydrophobizable intermetallic corn-pounds like isoferroplatinum or moncheite, or other telluride PGM-containing minerals. Further examples of separable PGM minerals in form of sulfide, hydrophobizable intermetallic, arsenide or telluride minerals can be found e.g. in a review article "Platinum Group Metals and compounds", in "Ullmann's Encyclopaedia of Industrial Chemistry", 2005 Wiley-VCH Verlag GmbH & Co. KGaA, Weinheim, doi: 10.1002/14356007.a21 075, Chapter 3, page 9.

The at least one hydrophilic metal compound is preferably selected from the group consisting of oxidic and hydroxidic metal compounds, for example silicon dioxide $SiO_2$, silicates, aluminosilicates, for example feldspars, for example albite $Na(Si_3Al)O_8$, mica, for example muscovite $KAl_2[(OH,F)_2AlSi_3O_{10}]$, Garnets (Mg, Ca, $Fe^{II}$)$_3$(Al, $Fe^{III}$)$_2$(SiO$_4$)$_3$, $Al_2O_3$, FeO(OH), $FeCO_3$, $Fe_2O_3$, $Fe_3O_4$ and further related minerals and mixtures thereof.

Examples of sulfidic ores which can be used according to the invention are, for example, selected from the group of copper ores consisting of covellite CuS, molybdenum(IV) sulfide, chalcopyrite (cupriferous pyrite) $CuFeS_2$, bornite $Cu_5FeS_4$, chalcocite (copper glass) $Cu_2S$ and mixtures thereof.

Suitable oxidic metal compounds which can be used according to the invention are preferably selected from the group consisting of silicon dioxide $SiO_2$, silicates, aluminosilicates, for example feldspars, for example albite $Na(Si_3Al)O_8$, mica, for example muscovite $KAl_2[(OH,F)_2AlSi_3O_{10}]$, garnets (Mg, Ca, $Fe^{II}$)$_3$(Al, $Fe^{III}$)$_2$(SiO$_4$)$_3$, plagioclase feldspar, orthopyroxene, olivine, clay minerals and further related minerals and mixtures thereof.

Accordingly, ore mixtures obtained from mines are preferably used in the process of the invention, According to a further preferred embodiment, the process according to the present invention is conducted in order to separate slag, for example smelter slag or furnace slag. These materials are in general known to the skilled artisan.

In a preferred embodiment, the slag which is treated according to the present invention, is selected from furnace slag, for example resulting from processing concentrates from platinum group metals (PGMs) bearing ores, spent catalyst materials or mixtures thereof.

The slag, preferably furnace slag, which is preferably employed in the process according to the present invention is preferably obtained from melting processes known to the skilled artisan, for example to obtain metals like Mo, Cu, Ni, Ag, Hg, Au, Pt, Pd, Rh, Ru, Ir, Os or mixtures thereof. For example, electric arc smelting is used in these furnaces and is further employed in process such as smelting of scrap iron.

In a preferred embodiment the at least one metal which is to be separated from the slag according to the present invention is selected from the group consisting of Ag, Au, Pt, Pd, Rh, Ru, Ir, Os, Cu, Mo, Ni, Mn, Zn, Pb, Te, Sn, Hg, Re, V, Fe and mixtures thereof. In principle, these metals may be present in elemental form or as compounds, for example in oxidic and/or sulfidic form, as a binary compound or a component in a multimetal compound. In a further embodiment of the present invention the mentioned precious metals are present in form of metal compounds, like for example, alloys with other metals e. g. Fe, Cu, Ni, Pb, Bi, with each other, and/or compounds with nonmetals e.g. phosphides, arsenides, sulphides, selenides, tellurides etc. Particularly preferred metal compounds are metal alloys.

Preferably the present invention relates to the process according to the present invention, wherein the at least metal is selected from the group consisting of Au, Pt, Ir, Pd, Os, Ag, Hg, Rh, Ru and mixtures thereof, in particular Au, Pt, Pd, Rh, further preferred Pt, Pd, Rh.

In a preferred embodiment of the present invention, the slag, preferably the furnace slag, that is used is a solid solution and preferably comprises further components selected from the group consisting of $SiO_2$, CaO, $Al_2O_3$, MgO, $P_2O_3$, $ZrO_2$, $Fe_2O_3$, $Fe_3O_4$, $CeO_2$, $Cr_2O_3$, complex oxide matrices and mixtures thereof. These oxides are not necessarily present in the slag matrix as isolated compounds, but may only be present as complex oxides. It is common to represent a mixed metal oxide as comprised of binary oxides of the respective metals. In this text, this nomenclature shall be used. Said solid solution may be amorphous and/or glass-like, or may contain crystalline material comprised of metal oxides listed above.

A very typical composition of a furnace slag that can particularly preferably be used in the process according to the present invention comprises 5 to 80% by weight $SiO_2$, 20 to 50% by weight CaO, 0 to 60% by weight $Al_2O_3$, 0 to 10% by weight MgO, 0 to 10% by weight $P_2O_5$, 0 to 10% by weight $ZrO_2$, 0 to 10% by weight $Fe_2O_3$, and optionally other iron oxides, 0 to 10% by weight $CeO_2$, and optionally other components.

In a preferred embodiment of the process of the invention, the mixture comprising at least one first material and at least one second material in step (A) is in the form of particles having a size of from 100 nm to 100 μm, see, for example U.S. Pat. No. 5,051,199. In a preferred embodiment, this particle size is obtained by milling. Suitable processes and apparatuses are known to those skilled in the art, for example wet milling in a ball mill. The mixture comprising at least one first material and at least one second material is therefore milled to particles having a size of from 100 nm to 100 μm before or during step (A) in a preferred embodiment of the process of the invention. Preferred ore mixtures comprising metals like Mo, Cu, Au and/or Ag have a content of sulfidic minerals of 0.1 to 10% by weight, preferably 0.4 to 1.0% by weight. For platinum group metals (PGM) like Ru, Rh, Pd, Pt, Os and Ir, the content of PGM containing minerals like sulfides, arsenides, tellurides or intermetallic compounds may be significantly lower, e.g. 0.3 to 20 ppm by weight, preferably 0.6 to 2 ppm by weight.

Examples of sulfidic minerals which are present in the mixtures which can be used according to the invention are those mentioned above. In addition, sulfide of metals other than copper, for example, sulfides of iron, lead, zinc or molybdenum, i.e. $FeS/FeS_2$, PbS, ZnS or $MoS_2$, can also be present in the mixtures. Furthermore, oxidic compounds of metals and semimetals, for example silicates or borates or other salts of metals and semimetals, for example phosphates, sulfates or oxides/hydroxides/carbonates, and further salts, for example azurite $[Cu_3(CO_3)_2(OH)_2]$, malachite $[Cu_2[(OH)_2(CO_3)]]$, barite $(BaSO_4)$, monazite $((La-Lu)PO_4)$, can be present in the ore mixtures to be treated according to the invention. Further examples of the at least one first material which is separated off by the process of the invention are noble metals, for example Au, Pt, Pd, Rh, etc., preferably in the native state.

A typical ore mixture which can be separated by means of the process of the invention has the following composition: about 30% by weight of $SiO_2$, about 10% by weight of $Na(Si_3Al)O_8$, about 3% by weight of $Cu_2S$, about 1% by weight of $MoS_2$, balance chromium, iron, titanium and magnesium oxides. If ore mine tailings are treated according to the present invention, the amount of copper may be lower, e.g. 0.1 to 0.3% by weight $Cu_2S$, for example 0.2% by weight $Cu_2S$.

For the purposes of the present invention, "surface-modifying substance" means a substance which is able to alter the surface of the particle to be separated off in the presence of other particles which are not to be separated off in such a way that attachment of a hydrophobic particle occurs as a result of hydrophobic interactions, ionic forces, van der Waals interactions and/or other attractive forces. Surface-modifying substances which can be used according to the invention selectively attach or bind to the at least one first material and thereby make the first material suitably hydrophobic. "Selectively" means, for the purposes of the present invention, that the partition coefficient of the surface-modifying substance between the surface of the at least one first material and the surface of the at least one second material is generally >1, preferably >100, particularly preferably >10 000, i.e. the surface-modifying substance preferentially binds to the surface of the at least one first material and not to the surface of the at least one second material.

For example, if the surface-modifying substance is a collector, it preferentially binds to the surface of the at least one valuable matter containing material (first material) compared to the surface of the at least one second material. In an alternative example, the hydrophobizing agent preferentially binds to the surface of the magnetic particle (first material) compared to the surface of the at least one second material.

In one embodiment of the present invention, the process of the invention is preferably carried out using a surface-modifying substance of the general formula (III')

$$A'\text{-}Z' \qquad (III')$$

which binds to the at least one first material, where

A' is selected from among linear or branched $C_2$-$C_{30}$-alkyl, $C_2$-$C_{30}$-heteroalkyl, optionally substituted $C_6$-$C_{30}$-aryl, optionally substituted $C_6$-$C_{30}$-heteroalkyl, $C_6$-$C_{30}$-aralkyl and Z is a group by means of which the compound of the general formula (III') binds to the at least one hydrophobic material.

Heteroatoms which may be present according to the invention are selected from among N, O, P, S, Si and halogens such as F, Cl, Br and I.

In a particularly preferred embodiment. A' is a linear or branched $C_2$-$C_{12}$-alkyl, very particularly preferably a linear $C_2$-$C_5$-alkyl, in particular a $C_2$- or $C_4$-alkyl, or a $C_8$-alkyl.

In a further preferred embodiment, A' is preferably a linear or branched, preferably linear, $C_6$-$C_{20}$-alkyl. Furthermore, A' is preferably a branched $C_6$-$C_{14}$-alkyl in which the at least one substituent, preferably having from 1 to 6 carbon atoms, is preferably present in the 2 position, for example 2-ethylhexyl and/or 2-propylheptyl.

In a further particularly preferred embodiment, Z' is selected from the group consisting of anionic groups $-(X)_n-PO_3^{2-}$, $-(X)_n-PO_2S^{2-}$, $-(X)_n-POS_2^{2-}$, $-(X)_n-PS_3^{2-}$, $-(X)_n-PS_2^-$, $-(X)_n-POS^-$, $-(X)_n-PO_2^-$, $-(X)_n-PO_3^{2-}-(X)_n-CO_2^-$, $-(X)_n-CS_2^-$, $-(X)_n-COS^-$, $-(X)_n-C(S)NHOH$, $-(X)_n-S^-$ where X is selected from the group consisting of O, S, NH, $CH_2$ and n=0, 1 or 2, if appropriate with cations selected from the group consisting of hydrogen, $NR_4^+$ where the radicals R are each, independently of one another, hydrogen or $C_1$-$C_8$-alkyl, an alkali metal or alkaline earth metal. The anions mentioned and the corresponding cations form, according to the invention, uncharged compounds of the general formula (III').

If n=2 in the formulae mentioned, then two identical or different, preferably identical, groups A' are bound to a group Z'.

In a particularly preferred embodiment, use is made of compounds selected from the group consisting of xanthates A'-O-$CS_2^-$, dialkyldithiophosphates $(A'-O)_2$-$PS_2^-$, dialkyldithiophosphinates $(A')_2$-$PS_2^-$ and mixtures thereof, where the radicals A' are each, independently of one another, a linear or branched, preferably linear, $C_6$-$C_{20}$-alkyl, preferably n-octyl, or a branched $C_6$-$C_{14}$-alkyl in which the branch is preferably present in the 2 position, for example 2-ethylhexyl and/or 2-propylheptyl. Counterions present in these compounds are preferably cations selected from the group consisting of hydrogen, $NR^{12}_4^+$ where the radicals $R^{12}$ are each, independently of one another, hydrogen or $C_1$-$C_8$-alkyl, an alkali or alkaline earth metal, in particular sodium or potassium.

Very particularly preferred compounds of the general formula (III') are selected from the group consisting of sodium or potassium ethyl xanthate, sodium or potassium n-octylxanthate, sodium or potassium butylxanthate, sodium or potassium di-n-octyldithiophosphinate, sodium or potassium di-n-octyldithiophosphate, sodium, ammonium or potassium salts of 2-ethyl-hexylxanthate, dixanthogenates and mixtures of these compounds.

In the case of noble metals, for example Au, Pd, Rh etc., particularly preferred surface-active substances are monothiols, dithiols and trithiols or 8-hydroxyquinolines, for example as described in EP 1 200 408 B1 and potassium salts of 2-ethyl-hexylxanthate and mixtures of these compounds.

In the case of metal oxides, for example FeO(OH), $Fe_3O_4$, ZnO etc., carbonates, for example azurite $[Cu(CO_3)_2(OH)_2]$, malachite $[Cu_2[(OH)_2CO_3]]$, particularly preferred surface-modifying substance are octylphosphonic acid (OPA), $(EtO)_3Si$-A, $(MeO)_3Si$-A', with the abovementioned meanings for A'. In a preferred embodiment of the process of the invention, no hydroxamates are used as surface-active substances for modifying metal oxides.

In the case of metal sulfides, for example $Cu_2S$, $MoS_2$, etc., particularly preferred surface-modifying substance are monothiols, dithiols and trithiols or xanthogenates.

In a further preferred embodiment of the process of the invention. Z' is $-(X)_n-CS_2^-$, $-(X)_n-PO_2^-$ or $-(X)_n-S^-$ where X is O and n is 0 or 1 and a cation selected from among hydrogen, sodium and potassium. Very particularly preferred surface-modifying substance are 1-octanethiol, potassium n-octylxanthate, potassium butylxanthate, octylphosphonic acid or a compound of the formula (IV)

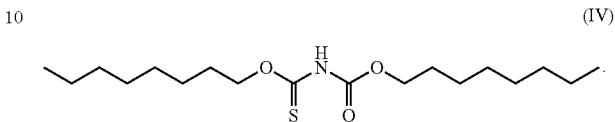

The at least one surface-modifying substance is generally used in an amount which is sufficient to achieve the desired effect. In a preferred embodiment, the at least one surface-modifying substance is added in an amount of from 0.0005 to 5% by weight, in each case based on the total solid present in the mixture to be treated.

According to a preferred embodiment of the process according to the present invention, the at least one surface-modifying substance is a compound of the general formula (III) or derivative thereof $$[(A)_m(Z)_n]_o \quad (III)$$

wherein each A is independently selected from linear or branched $C_1$-$C_{30}$-alkyl, $C_2$-$C_{30}$-alkenyl $C_1$-$C_{30}$-heteroalkyl, optionally substituted $C_6$-$C_{30}$-aryl, $C_6$-$C_{30}$-cycloalkyl, $C_6$-$C_{30}$-heteroalkyl, $C_6$-$C_{30}$-heterocycloalkyl, $C_6$-$C_{30}$-aralkyl, each of which may be unsubstituted or optionally substituted;

and each Z is independently selected from anionic groups, cationic groups or non-ionic groups;

m is an integer number of 1, 2, 3, 4, 5, 6, 7, 8, 9 or 10;

n is an integer number of 1, 2, 3, 4, 5, 6, 7, 8, 9 or 10; and o is an integer number of 1, 2, 3, 4, 5, 6, 7, 8, 9 or 10 to 100.

It is understood that formula (III) includes all possible combinations of how each A and each Z may be attached to one another. This includes any linear attachment, such as in -A-A-Z-Z-, A-Z-A-Z-, —Z-A-Z-A- and the like; branched attachments, such as in

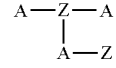

and the like; and circular attachments such as in

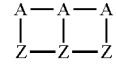

and the like. The skilled person is able to identify suitable attachment sites, such as substitution sites, in substituent A and Z that allow the attachment.

Furthermore, particularly preferred attachment sites are indicated in the respective definition of substituent Z.

In a particularly preferred embodiment. A is a linear or branched $C_1$-$C_{14}$-alkyl, and preferably a linear $C_4$-alkyl or $C_8$-alkyl.

In a further preferred embodiment, A is preferably a branched $C_1$-$C_{20}$-alkyl, particularly preferably a branched $C_6$-$C_{14}$-alkyl, wherein preferably at least one branch, preferably a branch having 1 to 6 carbon atoms, is attached in 2-position, such as in 2-ethylhexyl and/or 2-propylheptyl. Corresponding compounds being substituted in 2-position are, for example, obtained using the Guerbet reaction that is known to the skilled artisan as one reaction step.

In a preferred embodiment, Z is selected as an anionic group. Non-limiting examples of anionic groups are

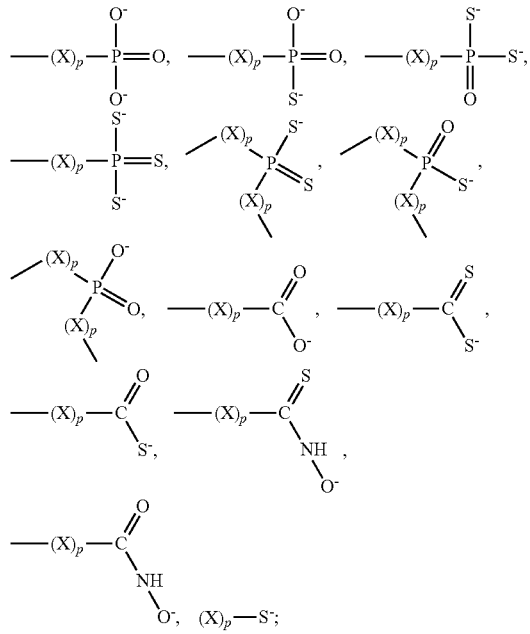

wherein each X is independently selected from the group consisting of O, S, NH, $CH_2$; and each p is independently selected from 0, 1 or 2.

In a preferred embodiment, the anionic group is present as a salt with at least one cation where-in preferably the at least one cationic counter ion is selected from the group consisting of hydrogen, $N(R^{11})_4^+$; wherein each $R^{11}$ is independently selected from hydrogen, $C_1$-$C_8$-alkyl, hydroxy-substituted $C_1$-$C_8$-alkyl or $C_1$-$C_8$-heteroalkyl, preferably HO—$CH_2CH_2$— or HO—$CH_2CH_2$—O—$CH_2CH_2$—; alkali- or earth alkali metals, preferably sodium or potassium; or combinations thereof.

The negatively charged anionic groups may of course also be present in a protonated form, depending, for example, on the pH of the aqueous environment. For example, the —$(X)_p$—$S^-$ anion group may be present as a —$(X)_p$—SH neutral group.

In another preferred embodiment, Z is selected as a cationic group. Non-limiting examples of cationic groups include, but are not limited to,

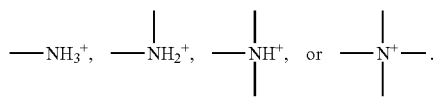

The cationic group may of course also be present in a deprotonated form, depending, for example, on the pH. For instance, —$NH_3^+$ may also be present as —$NH_2$.

In another preferred embodiment, Z is selected as a non-ionic group. Examples of non-ionic groups include, but are not limited to, —$X_A$—,

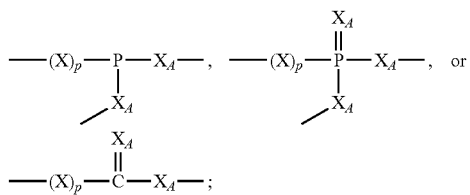

wherein each X is defined as indicated above and each $X_A$ is independently O or S, In a preferred embodiment, the at least one surface-modifying substance is a compound of formula (IIIA) or derivative thereof $$A\text{-}Z_1\text{-}A \tag{IIIA}$$

wherein each A is selected as described above and wherein $Z_1$ is selected from the group consisting of

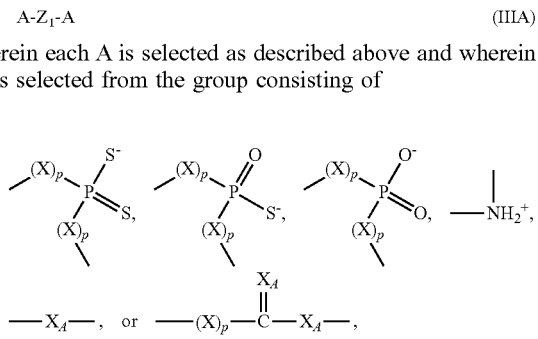

wherein X, $X_A$ and p are defined as described above.

In another preferred embodiment, the at least one surface-modifying substance is a compound of formula (IIIB) or derivative thereof $$A\text{-}Z_1\text{-}A\text{-}Z_2 \tag{IIIB}$$

wherein A and $Z_1$ are defined as described above and wherein $Z_2$ is selected from the group consisting of

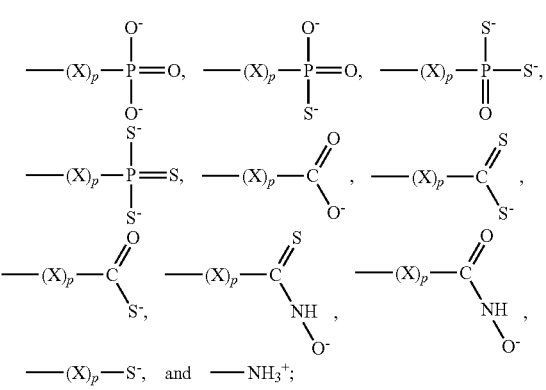

and
wherein X and p are as defined above.

In yet another preferred embodiment, the at least one surface-modifying substance is a compound of formula (IIIC) or derivative thereof

wherein A is selected as defined above and wherein $Z_3$ is selected from the group consisting of

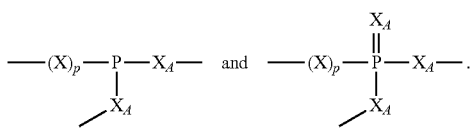

In yet another preferred embodiment, the at least one surface-modifying substance is a compound of formula (IIID) or formula (IIIE),

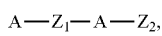 (IIID)

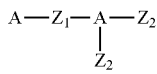 (IIIE)

wherein A, $Z_1$, and $Z_2$ are defined as described above.

In yet another embodiment, the at least one surface-modifying substance is a compound of formula (IIIF) or (IIIG) or derivatives thereof

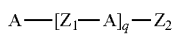 (IIIF)

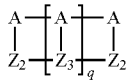 (IIIG)

wherein q is an integer of 1, 2, 3, 4 or 5 to 100 and A, $Z_1$, $Z_2$ or $Z_3$ are defined as described above.

In a further preferred embodiment, the at least one surface-modifying substance is selected from (i) xanthates, preferably xanthates of formula (IIIH) or (IIIJ) or derivatives thereof

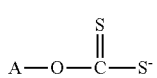 (IIIH)

 (IIIJ)

(ii) dithiophosphates, preferably dithiophosphates of formula (IIIK) or derivatives thereof

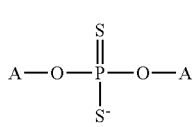 (IIIK)

(iii) dithiophosphinates, preferably dialkyldithiophosphinates of formula (IIIL) or derivatives thereof

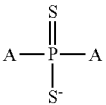 (IIIL)

(iv) dialkyldithiocarbamates, preferably dialkyldithiocarbamates of formula (IIIM) or derivatives thereof

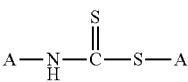 (IIIM)

(v) alkyltrithiocarbamates preferably alkyltrithiocarbamates of formula (IIIN) or derivatives thereof

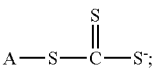 (IIIN)

or mixtures thereof, wherein each A is defined as described above. In a preferred embodiment, each A is independently selected from a group consisting of a linear or branched and preferably linear $C_6$-$C_{20}$-alkyl, more preferably n-octyl; or a branched $C_6$-$C_{14}$-alkyl, wherein the branch is preferably located in 2-position, for example 2-ethylhexyl and/or 2-propylheptyl.

In an especially preferred embodiment, the at least one surface-modifying substance is selected from the group consisting of sodium- or potassium-n-octylxanthate, sodium- or potassium-butylxanthate, sodium- or potassium-di-n-octyldithiophosphinate, sodium- or potassium-di-n-octyldithiophosphate, sodium- or potassium-di-n-octyldithiocarbamates, sodium- or potassium-ethyl-hexyl-xanthate and mixtures thereof.

In a particularly preferred embodiment, the at least one surface-modifying substance is selected from the group consisting of potassium-n-octyl xanthate (1:1 salt of carbonodithionic acid O-ocytyl ester) or potassium-di-n-octyl-dithiophosphinate or mixtures thereof.

In a preferred embodiment, preferred surface-modifying substance for valuable matter containing material wherein the at least one valuable matter is a noble metal, such as Au, Pd, Rh, etc., are monothiols, dithiols and trithiols, or 8-hydroxyquinolines and preferably, the monothiols, dithiols and trithiols, or 8-hydroxyquinolines as described in EP 1 200 408.

In another preferred embodiment, preferred surface-modifying substance for valuable matter containing material wherein the at least one valuable matter is a metal sulfide, such as $Cu_2S$, $MoS_2$, $FeS_2$ etc., are monothiols, dithiols and trithiols, xanthates or dithiophosphates.

In a preferred embodiment, the at least one surface-modifying substance is used in an amount which is sufficient to achieve the desired effect. In a preferred embodiment, the at least one collector is added in an amount of from about 0.0001 to about 1% by weight and preferably from about 0.001 to about 0.1% by weight in each case based on the weight of total dry solid content.

Step (B):

Optional Step (B) of the process according to the present invention comprises addition of at least dispersion medium to the mixture or dispersion of step (A).

The mixture obtained in step (A) comprises, in one embodiment, at least one dispersion medium, agglomerates of at least one first material and at least one magnetic particle, at least one second material and, if appropriate, surface-modifying substances, polymeric compounds, etc., depending on which embodiment has been carried out in step (A).

Step (B) can be carried out, i.e. further dispersion medium is added, in order to obtain a dispersion having a lower concentration.

Suitable dispersion media are all dispersion media which have been mentioned above with regard to step (A). In a particularly preferred embodiment, the dispersion medium in step (B) is water.

In general, the amount of dispersion medium added in step (A) and optionally in step (B), according to the invention, can be selected so that a dispersion which is readily stirrable and/or conveyable is obtained. In a preferred embodiment, the amount of mixture to be treated based on the total slurry or dispersion is up to about 90% by weight, particularly preferably from about 5 to about 50% by weight. In another embodiment, the amount to be treated is from about 5 to about 40% by weight solid content wherein the solid content is based on the total amount of solids present.

In a preferred embodiment of the process of the invention, step (B) is not carried out but instead step (A) is carried out from the beginning in an aqueous dispersion having an appropriate solid content or concentration.

The optional addition of dispersion medium in step (B) of the process of the invention can, according to the invention, be carried out by all methods known to those skilled in the art.

Step (C):

Step (C) of the process of the invention comprises treatment of the dispersion from step (A) or (B) with at least one core-shell-particle according to the present invention, wherein the at least one metal or a compound thereof, the at least one semimetal or a compound thereof or a mixture of two or more thereof is magnetic, and the at least one first material to which the at least one surface-modifying substance is attached and the at least one core-shell-particle form an agglomerate. As used herein, the agglomerate may also be referred to as an addition product, Core-shell-particles according to the present invention that are used in step (C) of the process according to the present invention are explained in detail above.

According to a preferred embodiment of the process according to the present invention, step (A), bringing the at least one first material comprised in the mixture into contact with a surface-modifying substance in order to hydrophobicize the at least one first material, is conducted before step (C), bringing this mixture into contact with at least one magnetic core-shell-particle so that the at least one magnetic core-shell-particle and the at least one first material which has been hydrophobicized on the surface agglomerate.

According to a further preferred embodiment of the process according to the present invention, step (C), bringing the at least one magnetic core-shell-particle is contacted first with the at least one first material comprised in the mixture, is conducted before step (A), addition of at least one surface-modifying substance, so that the at least one magnetic core-shell-particle and the at least one first material which has been hydrophobicized on the surface agglomerate, According to a further preferred embodiment the mixture comprising at least one first material and the at least one second material is contacted with at least one magnetic material and at least one surface-modifying substance, steps (A) and (C), at the same time, so that the at least one magnetic core-shell-particle and the at least one first material which has been hydrophobicized on the surface agglomerate.

The treatment of the solution or dispersion with at least one hydrophobic magnetic core-shell-particle in step (C) of the process of the invention can be carried out by all methods known to those skilled in the art.

In a preferred embodiment, the at least one magnetic core-shell-particle is dispersed in a suitable dispersion medium.

Suitable dispersion media are all dispersion media in which the at least one magnetic core-shell-particle is not completely soluble. Suitable dispersion media for dispersion as per step (C) of the process of the invention are selected from the group consisting of water, water-soluble organic compounds and mixtures thereof, particularly preferably water. Particular preference is given to using the same dispersion medium in step (C) as in step (B). Further preferred dispersion media of the core-shell-particles according to the present invention are aqueous solutions of surfactants, preferably of non-ionic surfactants, having for example a concentration of 0.01 to 1% by weight, preferably 0.05 to 0.5% by weight.

According to the invention, the amount of dispersion medium for predispersing the magnetic core-shell-particles can generally be selected so that a slurry or dispersion which is readily stirrable and/or conveyable is obtained. In a preferred embodiment, the amount of mixture to be treated based on the total slurry or dispersion is up to 60% by weight.

According to the invention, the dispersion of the magnetic core-shell-particles can be produced by all methods known to those skilled in the art. In a preferred embodiment, the magnetic core-shell-particles to be dispersed and the appropriate amount of dispersion medium or mixture of dispersion media are combined in a suitable reactor, for example a glass reactor, and stirred by means of devices known to those skilled in the art, for example in a glass tank by means of a magnetically operated propeller stirrer, for example at a temperature of from 1 to 80° C., preferably at room temperature.

The treatment of the dispersion with at least one magnetic core-shell-particle is generally carried out by combining the two components by methods known to those skilled in the art. In a preferred embodiment, a dispersion of the at least one magnetic core-shell-particle is added to the mixture which has previously been treated with at least one surface-modifying substance. In a further embodiment, the magnetic particle in solid form can be added to a dispersion of the mixture to be treated. In a further preferred embodiment, both components are present in dispersed form.

Step (C) is generally carried out at a temperature of from 1 to 80° C., preferably from 10 to 40° C.

In step (C), the at least one magnetic core-shell-particle becomes attached to the hydrophobic material of the mixture to be treated. This attachment between the two components is based on hydrophobic interactions. There is generally no bonding interaction between the at least one magnetic core-shell-particle and the hydrophilic component of the mixture, so that these components do not become attached to one another. Thus, agglomerates (i.e. addition products) of the at least one hydrophobic material and the at least one magnetic core-shell-particle are present alongside the at least one hydrophilic material in the mixture after step (C).

Step (D):

Step (D) of the process of the invention comprises separation of the agglomerate (addition product) from step (C) from the mixture by application of a magnetic field.

Step (D) can, in a preferred embodiment, be carried out by introducing a permanent magnet into the reactor in which the mixture from step (C) is present. In a preferred embodiment, a dividing wall composed of non-magnetic material, for example the glass wall of the reactor, is present between the permanent magnet and mixture to be treated. In a further preferred embodiment of the process of the invention, an electromagnet which is only magnetic when an electric current flows is used in step (D). Suitable apparatuses are known to those skilled in the art.

Step (D) of the process of the invention can be carried out at any suitable temperature, for example from 10 to 60° C.

During step (D), the mixture is preferably continuously stirred by means of a suitable stirrer, for example a Teflon stirrer bar or a propeller stirrer.

In step (D), the addition product from step (C) can, if appropriate, be separated off by all methods known to those skilled in the art, for example by draining the liquid together with the hydrophilic component of the suspension from the reactor used for step (D) via the bottom valve or pumping the components of the suspension which are not held back by the at least one magnet away through a hose.

Step (E):

In one embodiment of the process of the present invention, step (E) comprises cleavage of the agglomerate (addition product) which has been separated off in step (D) to obtain the at least one first material and the at least one magnetic core-shell-particle separately. In a preferred embodiment of the process of the invention, the cleavage in step (E) is carried out in a non-destructive manner, i.e. the individual components present in the dispersion are not changed chemically. For example, the cleavage according to the invention is not affected by oxidation of the hydrophobicizing agent, for example to give the oxidation products or degradation products of the hydrophobicizing agent.

Cleavage can be carried out by all methods known to those skilled in the art which are suitable for cleaving the addition product in such a way that the at least one magnetic particle can be recovered in reusable form. In a preferred embodiment, the magnetic particle which has been cleaved off is reused in step (C).

In a preferred embodiment, the cleavage in step (E) of the process of the invention is effected by treatment of the agglomerate (addition product) with a substance selected from the group consisting of organic solvents, basic compounds, acidic compounds, oxidants, reducing agents, surface-active substances and mixtures thereof.

Examples of suitable organic solvents are alcohols, such as methanol, ethanol, propanol, for example n-propanol or isopropanol; aromatic solvents, for example benzene, toluene, xylenes; ethers, for example diethyl ether, methyl t-butyl ether; ketones, for example acetone; aromatic or aliphatic hydrocarbons, for example saturated hydrocarbons with for example 6 to 10 carbon atoms, for example dodecane and/or Shellsol®, Diesel fuel and mixtures thereof. The main components of Diesel fuel are predominantly alkanes, cycloalkanes and aromatic hydrocarbons having about 9 to 22 carbon atoms per molecule and a boiling range between 170° C. and 390° C.

Examples of basic compounds which can be used according to the invention are aqueous solutions of basic compounds, for example aqueous solutions of alkali metal and/or alkaline earth metal hydroxides, for example KOH, NaOH, lime water, aqueous ammonia solutions, aqueous solutions of organic amines of the general formula $R^{10}{}_3N$, where the radicals $R^{10}$ are selected independently from the group consisting of $C_1$-$C_8$-alkyl which may optionally be substituted by further functional groups. In a preferred embodiment, step (D) is carried out by addition of aqueous NaOH solution to a pH of about 13, for example in order to separate off $Cu_2S$ modified with octyl phosphonic acid (OPA). The acidic compounds can be mineral acids, for example HCl, $H_2SO_4$, $HNO_3$ or mixtures thereof, organic acids, for example carboxylic acids. As oxidants, it is possible to use $H_2O_2$, for example as 30% strength by weight aqueous solution (Perhydrol). The separation of $Cu_2S$ modified with thiols is preferably carried out using $H_2O_2$ or $Na_2S_2O_4$.

Examples of surface-modifying substances which can be used according to the invention are nonionic, anionic, cationic and/or amphoteric (zwitterionic) surfactants.

In a preferred embodiment, the addition product of hydrophobic material and magnetic particle is cleaved by means of a cationic, anionic or non-ionic surfactant or an organic solvent, particularly preferably by means of a non-ionic surfactant. This process can also be aided mechanically. In a preferred embodiment, ultrasound is used for aiding the cleavage process.

In general, the organic solvent is used in an amount which is sufficient to cleave virtually all of the agglomerate (addition product). In a preferred embodiment, from 20 to 100 ml of organic solvent are used per gram of addition product of hydrophobic material and magnetic particle to be cleaved.

After cleavage, the at least one first material and the at least one magnetic core-shell-particle are, according to the invention, present as dispersion in the abovementioned cleavage reagent, preferably an organic solvent.

The at least one magnetic core-shell particle can be separated from the dispersion comprising this at least one magnetic core-shell-particle and the at least one first material by means of a permanent magnet or electromagnet. Details of the separation are analogous to step (D) of the process of the invention.

The present invention therefore preferably relates to the process as mentioned above, wherein after cleavage according to step (E) the at least one magnetic core-shell particle is separated from the dispersion comprising this at least one magnetic core-shell-particle and the at least one first material by means of a permanent magnet or electromagnet.

Due to the very specific silicon comprising polymer that is present in the shell of the core-shell-particles, in particular in the magnetic core-shell-particles according to the present invention, these core-shell-particles show a very high stability under the conditions of the separation process according to the present invention, Therefore, the core-shell-particles according to the present invention can advantageously be reused in the separation process, preferably without significant loss of hydrophobicity at the surface. In one embodiment, after a agglomeration/deagglomeration cycle at least about 70% of the core-shell-particles originally used in said cycle can be recovered. In another embodiment, at least about 75%, at least about 80% or at least about 85% of the core-shell-particles originally used in said cycle can be recovered.

The first material to be separated off, preferably the metal compound to be separated off, is preferably separated from the organic solvent by distilling off the organic solvent. The first material which can be obtained in this way can be purified by further processes known to those skilled in the art. The solvent can, if appropriate after purification, be recirculated to the process of the invention.

The present invention further relates to the process as mentioned above, wherein after step (D) the following step (F) is conducted:

(F) further processing of the particles or of the agglomerate from step (D) via smelting, extracting and/or wet chemical refining and no step (E) is conducted.

The magnetic particles or agglomerates obtained in step (D) preferably comprise iron comprising magnetic substances or magnetic particles in addition to at least one metal, being preferably at least one precious metal. Because iron is essentially necessary for melting and/or smelting processes to obtain the at least one metal in pure form, the particles or agglomerates that are obtained in step (D) of the process according to the present invention can directly be treated in a smelting and/or melting process.

In the case that precious metals are used as first material in combination with iron comprising magnetic particles, no need for further addition of other iron containing compounds exists. Instead, the magnetic iron oxide particles loaded with precious metals are added to the furnace feed in place of iron oxide otherwise added to the process.

Definitions

As used herein, the term "valuable matter" refers to any material that may be of commercial value. Examples of valuable matter include, but are not limited to, elemental metals such as Ag, Au, Pt, Pd, Rh, Ru, Ir, Os, Cu, Mo, Ni, Mn, Zn, Pb, Te, Sn, Hg, Re, V, Fe or mixtures thereof. In a preferred embodiment, the valuable matter includes PGMs, Au, Ag, Cu, rare earths and the like. A "valuable matter containing material" refers a material that contains such a valuable matter in any form, such as in ore minerals, metals in pure form, alloys or mixtures thereof. For example, a valuable matter containing material may be an ore mineral comprising the valuable matter Pt.

As used herein, the term "dispersion" refers to material comprising more than one phase wherein at least one of the phases consists of finely divided phase domains, often in the colloidal size range, dispersed throughout a continuous phase.

As used herein, the term "derivative" such as in "a compound of formula (III) or derivatives thereof" preferably refers to salts, the protonated form or the deprotonated form of said compounds. Preferred salts as derivatives of a compound wherein the compound represents the anionic part of the salt include salts wherein the respective one or more cation of the salt is sodium, potassium, calcium, magnesium or $N(R^{12})_4^+$, wherein $R^{12}$ is an unsubstituted or substituted $C_1$-$C_{12}$-alkyl Preferred salts as derivatives of a compound wherein the compound is the cation include salts wherein the respective one or more anion of the salt is Cl, Br, I, F, carbonate, phosphate, sulphate, sulphide or hydroxide and the like. The person skilled in the art is aware that the protonated and/or deprotonated form of a compound may depend on the pH in a dispersion.

As used herein, the term "optionally substituted" refers to a group that is either unsubstituted or substituted, e.g. with 1, 2, 3, 4 or 5 substituents. Preferred substituents are F, Cl, Br, I, OH, SH, —COOH, —NH₂, —CN, —C(O)NH₂ (amido), —C(O)NHC(O)—$C_1$-$C_{30}$-alkyl (imido), —O—$C_1$-$C_{30}$-alkyl (ether), —C(O)-$C_1$-$C_{30}$-alkyl (aldehyde), (=O), —S—$C_1$-$C_{30}$-alkylthioether, —C(O)NHOH (hydroxamate) or —N($R_1$)—C(O)OH (carbamate).

As used herein, the term "$C_1$-$C_{30}$-alkyl" refers to linear or branched hydrocarbons having 1 to 30 carbon atoms (or the number of carbon atoms indicated, i.e, a $C_1$-$C_6$-alkyl refers to a linear or branched hydrocarbon having 1 to 6 carbon atoms, etc.). Non-limiting example of $C_1$-$C_{30}$ alkyl include, but are not limited to methyl, ethyl, propyl, isopropyl, n-butyl, isobutyl, tert-butyl, pentyl, in particular n-pentyl, isopentyl, tert-pentyl, n-hexyl, isohexyl, tert-hexyl, n-heptyl, isoheptyl, tert-heptyl, n-octyl, isooctyl, tert-octyl, nonyl, n-nonyl, isononyl, tert-nonyl, n-decyl, isodecyl, tert-decyl, undecyl, n-undecyl, isoundecyl, tert-undecyl, or dodecyl, n-dodecyl, isododecyl or tert-dodecyl.

As used herein, the term "alkylsubstituted" refers to a group that is substituted, e.g. with 1, 2, 3, 4 or 5 independently selected $C_1$-$C_{30}$-alkyl groups.

As used herein, the term "linear or branched $C_1$-$C_{18}$-alkyl" refers to linear or branched hydrocarbons having 1 to 18 carbon atoms. Non-limiting example of $C_1$-$C_{18}$ alkyl include, but are not limited to methyl, ethyl, propyl, isopropyl, n-butyl, isobutyl, tert-butyl, pentyl, in particular n-pentyl, isopentyl, tert-pentyl, n-hexyl, isohexyl, tert-hexyl, n-heptyl, isoheptyl, tert-heptyl, n-octyl, isooctyl, tert-octyl, nonyl, n-nonyl, isononyl, tert-nonyl, n-decyl, isodecyl, tert-decyl, undecyl, n-undecyl, isoundecyl, tert-undecyl, or dodecyl, n-dodecyl, isododecyl or tert-dodecyl.

As used herein, the term "$C_2$-$C_{30}$-alkenyl" refers to linear or branched hydrocarbons having 2 to 30 carbon atoms and at least one C=C double bond. Examples of alkenyl which are particularly preferred according to the invention are ethenyl (vinyl), propenyl, in particular n-propenyl, isopropenyl, butenyl, n-butenyl, isobutenyl, tert-butenyl, pentenyl, in particular n-pentenyl, isopentenyl, tert-pentenyl, hexenyl, in particular n-hexenyl, isohexenyl, tert-hexenyl, heptenyl, in particular n-heptenyl, isoheptenyl, tert-heptenyl, octenyl, in particular n-octenyl, isooctenyl, tert-octenyl, nonenyl, in particular n-nonenyl, isononenyl, tert-nonenyl, decenyl, in particular n-decenyl, isodecenyl, tert-decenyl, undecenyl, in particular n-undecenyl, isoundecenyl, tert-undecenyl, or dodecenyl, in particular n-dodecenyl, isododecenyl or tert-dodecenyl.

As used herein, the term "$C_1$-$C_{30}$-heteroalkyl" refers to linear or branched hydrocarbons having 1 to 30 carbon atoms and at least one heteroatom selected form the group consisting of N, O, P and S. The at least one heteroatom may be either the point of attachment, such as in -Het-CH₂—, part of the chain, such as in —CH₂-Het-CH₂—, or the heteroatom may be terminal, such as in —CH₂-Het, wherein "Het" denotes the heteroatom. In case the heteroatom is terminal, the free valences may be occupied by hydrogen or a $C_1$-$C_{30}$-alkyl group.

As used herein, the term "$C_6$-$C_{30}$-aryl" refers to aromatic carbocyclic rings of 6 to 30 ring members, including both mono, bi-, and tri-cyclic ring systems, Non-limiting examples of $C_6$-$C_{30}$-aryl include -indenyl, - phenyl, -naphthyl-, acenaphthyl- antranyl, -phenanthryl and the like.

As used herein, the term "$C_5$-$C_{12}$-aryl" refers to aromatic carbocyclic rings of 5 to 12 ring members, including both mono and bicyclic ring systems. Preferably the "$C_5$-$C_{12}$-aryl" is a "$C_6$-$C_{10}$-aryl". Non-limiting examples of $C_6$-$C_{10}$-aryl include -indenyl, phenyl, -naphthyl-, and the like.

As used herein, the term "$C_6$-$C_{30}$-cycloalkyl" refers to mono-, bi- or tricyclic saturated hydrocarbons having from 6 to 30 carbon atoms. Representative $C_5$-$C_{30}$-cycloalkyl include cyclohexyl, cecloheptyl, cycloodyl, cyclononyl, cyclodecyl, cycloundecyl and cyclododecyl.

As used herein, the term "$C_6$-$C_{30}$ heterocycloalkyl" refers to a 6 to 30-membered mono-, bi- or tricyclic heterocyclic ring which is either saturated, unsaturated, non-aromatic or aromatic. The heteroatom in the heterocycloalkyl may be selected from O, S, P and N, wherein the nitrogen may be quartarnized and the S may also be present in form of S(O) or $S(O)_2$.

As used herein, the term "$C_6$-$C_{30}$-aralkyl" refers to aromatic mono-, bi or tricyclic rings that are substituted with 1, 2, 3, 4 or 5 alkyl groups. Examples of $C_6$-$C_{30}$-arylalkyl include tolyl, xylyl, propylbenzyl and hexylbenzyl.

As used herein, the term "rare earth metal" refers to one of a set of seventeen chemical elements in the periodic table, namely the fifteen lanthanides plus scandium and yttrium.

As used herein, the term "ore" refers to a type of rock that contains valuable matter such as valuable metal that can be extracted from the rock. The ores may be extracted through mining. The ore may contain a desired material, such as an ore mineral, and also an undesired second material such as gangue.

As used herein, the term "mineral" or "ore mineral" refers to a naturally occurring substance that is solid inorganic and representable by a chemical formula, which is usually abiogenic and may have an ordered atomic structure. An ore mineral may carry a valuable matter. The ore mineral is different from a rock, which can be an aggregate of minerals and/or non-minerals. Examples of minerals include, but are not limited to, sulfides, oxides, halides, carbonates, sulfates, and phosphates of valuable metals.

As used herein, the term "slag", "artificially prepared slag", "metallurgical slag", "furnace slag" or "smelter slag" refer to the by-product of a smelting process.

The main use of a smelting process is to convert an ore, scrap or a material mixture containing different metals into a form from which the desired metals can be skimmed as a metal layer and the undesired metal oxides, e.g. silicates, alumina, etc., remain as the slag. During smelting, a silicate-rich liquid phase may separate from the heavier metal melt. The latter is flowing through dedicated openings in the melting vessel and is further processed. The phase separation is however not complete, but a fraction of the desired metal becomes trapped in the liquid slag phase and remains dispersed there after solidification resulting in a so-called "mixing layer".

In general, one can distinguish between oxidative and reductive smelter operation. The slag material that can be separated according to the present invention can either be obtained under reductive conditions or can be obtained under oxidative conditions. For example, slag produced in PGM recovery operations, for example in Pt mines or old catalyst reprocessing etc., is usually formed under reducing conditions, which are exemplarily explained in the following. The energy needed to heat the mass to beyond the melting point is in general provided by an external heating, e.g. gas burners, or an electric arc. Often, carbon or other reducing materials are added. The goal is to reduce noble metal compounds to metal state. Reduced metals and the oxidic phase are immiscible and demix. Slags produced under reductive conditions often contain residual PGMs as free metals or alloys with other transition metals, particularly iron. These alloys are often ferromagnetic and can be separated from the slag matrix by a magnetic field after liberation. The losses of PGM into slag are almost exclusively due to incomplete demixing of the liquid metal and liquid slag phases—no significant formation of PGM solid solution in the slag occurs.

In a smelter that is operated under reductive conditions, the most base metal sulphides remain as sulphides. Some metal species, e.g. PGMs, may also remain as the native metal or tend to migrate into the magnetic fraction. Magnetite is often fed into the smelter to support the formation of the slag. Platinum and also rhodium preferably feature this behaviour to migrate to the magnetic fraction thus after the smelting process these precious group metals are hidden in the magnetic fraction, which is preferably in the slag, as dopants.

Is a smelter operated under oxidative conditions, the base metals sulphides and also some native metals compounds are oxidized. In this case, the magnetic separation process according to the present invention is rarely used without pre-treatment. However, if a surface treatment, for example a selective sulphidization of the desired metal of value, is preferably executed, the magnetic separation process according to the present invention can be employed as described herein. Besides the preferred sulphidization, also other surface treatments can be used to convert the desired metal species into a sulphidic, native or magnetic form. These treatments are known to the skilled artisan.

As used herein, the term "ore-bearing slag" refers to slag that comprises ores, i.e. slag that inter alia comprises a valuable matter containing material such as an ore mineral. The ore-bearing slag may also comprise at least one second material such as gangue.

As used herein, the term "wet ore tailing" refers to a dispersion comprising ore as a "tailing", i.e. as the undesired fractions left over after the process of separating the valuable fraction from the uneconomic fraction of an ore. However, such tailings may still comprise at least one valuable matter containing material but also at least one second material.

As used herein, the term "semimetal" refers to semimetals or "metalloids" in general which are known to the skilled artisan. The term "semimetal" includes boron, silicon, germanium, arsenic, antimony, tellurium, carbon, aluminium, selenium, polonium and astatine. Preferably, the semimetal is selected from the group consisting of boron, silicon, germanium, arsenic, antimony and tellurium.

As used herein, the term "complex oxide matrices" refers to a mixed metal oxide such as binary or higher-level oxides of the respective metals. Examples of complex oxide matrices include, but are not limited to, Ti-Si oxides, Si-Cr oxides, Si-Zr oxides and the like. As used herein, the term "surface-modifying substance" refers to a compound that lower the surface tension (or interfacial tension) between two liquids or between a liquid and a solid. Surface modifying substances include, but are not limited to, anionic surfactants, nonionic surfactants, cationic surfactants, or amphoteric (zwitterionic) surfactants. The terms "surface-modifying agent", "surface active agent" and "surfactant" are used interchangeably in the context of the present invention.

As used herein, the term "magnetic" as used for example in "magnetic particles" or "magnetic core" includes, but is not limited to, ferromagnetism.

As used herein, the term "at least one silicon comprising polymer comprising repeat units of the general formula (I) —[$SiR^1(OR^2)$—O—]— (I)" includes silicon comprising polymers, wherein said repeat unit or a derivative thereof is used as a starting material or is part of an intermediate exhibiting groups at which further condensation to the final polymer may take place. In one aspect, the silicon comprising polymer comprises repeat unit of formula (I') —[$SiR^1$—$O_{1.5}$]—. The number of repeat units —[$SiR^1$—$O_{1.5}$]— in these is embodiments is preferably from 10 to about 1000 (e.g., —[$SiR^1$—$O_{1.5}$]]$_{100}$-. $R^1$ is defined in these embodiments as defined above for general formula (I).

The silicon comprising polymer of the present invention includes polymers and copolymers derived from monomers selected from the group consisting of:

(NaO)($CH_3$)Si(OH)$_2$, (NaO)($C_2H_5$)Si(OH)$_2$, (NaO)($C_5H_{11}$)Si(OH)$_2$, (NaO)($C_8H_{17}$)Si(OH)$_2$, (KO)($CH_3$)Si(OH)$_2$, (KO)($C_2H_5$)Si(OH)$_2$, (KO)($C_5H_{11}$)Si(OH)$_2$, (KO)($C_8H_{17}$)Si(OH)$_2$, ($NH_4$O)($CH_3$)Si(OH)$_2$, ($NH_4$O)($C_2H_5$)Si(OH)$_2$, ($NH_4$O)($C_5H_{11}$)Si(OH)$_2$, ($NH_4$O)($C_8H_{17}$)Si(OH)$_2$, (NaO)$_2$($CH_3$)Si(OH), (NaO)$_2$($C_2H_5$)Si(OH), (NaO)$_2$($C_5H_{11}$)Si(OH), (NaO)$_2$($C_8H_{17}$)Si(OH), (KO)$_2$($CH_3$)Si(OH), (KO)$_2$($C_2H_5$)Si(OH), (KO)$_2$($C_5H_{11}$)Si(OH), (KO)$_2$($C_8H_{17}$)Si(OH), ($NH_4$O)$_2$($CH_3$)Si(OH), ($NH_4$O)$_2$($C_2H_5$)Si(OH), ($NH_4$O)$_2$($C_5H_{11}$)Si(OH), ($NH_4$O)$_2$($C_8H_{17}$)Si(OH), (NaO)$_3$($CH_3$)Si, (NaO)$_3$($C_2H_5$)Si, (NaO)$_3$($C_5H_{11}$)Si, (NaO)$_3$($C_5H_{17}$)Si, (KO)$_3$($CH_3$)Si, (KO)$_3$($C_2H_5$)Si, (KO)$_3$($C_5H_{11}$)Si, (KO)$_3$($C_8H_{17}$)Si, ($NH_4$O)$_3$($CH_3$)Si, ($NH_4$O)$_3$($C_2H_5$)Si, ($NH_4$O)$_3$($C_5H_{11}$)Si, ($NH_4$O)$_3$($C_8H_{17}$)Si, (NaO)($CH_3$)$_2$Si(OH), (NaO)($C_2H_5$)$_2$Si(OH), (KO)($CH_3$)$_2$Si(OH), (KO)($C_2H_5$)$_2$Si(OH), (NaO)$_2$($CH_3$)$_2$Si, (NaO)$_2$($C_2H_5$)$_2$Si, (KO)$_2$($CH_3$)$_2$Si, (KO)$_2$($C_2H_5$)$_2$Si, $Ca^{2+}$[($O^-$)($CH_3$)Si(OH)$_2$]$_2$, $Ca^{2+}$[(O)($C_2H_5$)Si(OH)$_2$]$_2$, $Ca^{2+}$[($O^-$)($C_5H_{11}$)Si(OH)$_2$]$_2$, $Ca^{2+}$[($O^-$)($C_8H_{17}$)Si(OH)$_2$]$_2$, $Ca^{2+}$[($O^-$)($CH_3$)$_2$Si(OH)]$_2$, $Ca^{2+}$[($O^-$)($C_2H_5$)$_2$Si(OH)]$_2$, $Ca^{2+}$[($O^-$)$_2$($CH_3$)Si(OH)], $Ca^{2+}$[($O^-$)$_2$($C_2H_5$)Si(OH)], $Ca^{2+}$[($O^-$)$_2$($C_5H_{11}$)Si(OH)], $Ca^{2+}$[($O^-$)$_2$($C_8H_{17}$)Si(OH)], $Ca^{2+}$[($O^-$)$_2$($CH_3$)$_2$Si], $Ca^{2+}$[($O^-$)$_2$($C_2H_5$)$_2$Si] and combinations thereof.

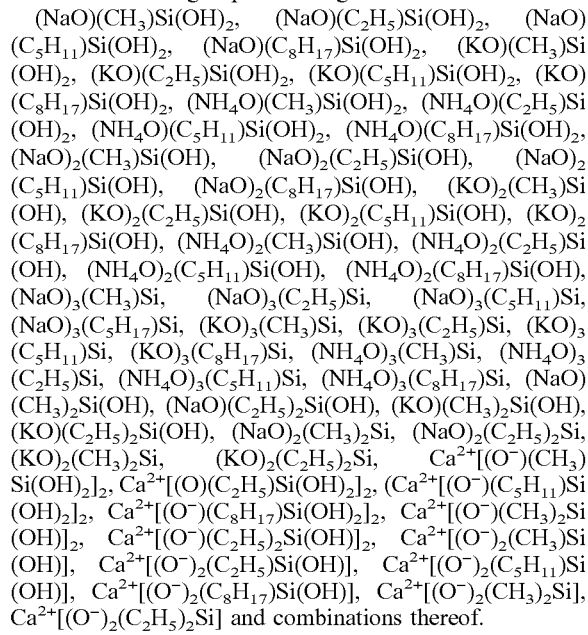

In one embodiment of this aspect a silicon comprising polymer of the present invention may be obtained from polymerization of potassium methyl siliconate in the presence of $CO_2$.

Suitable monomers and silicon comprising polymers are e.g. commercially available from Wacker Chemie AG under the tradename SILRES® (e.g. potassium methyl siliconate is available as SILRES® BS 16).

For the purposes of the present invention, "hydrophobic" as in "hydrophobic particle" or "hydrophobic substance" means that the corresponding particle can be hydrophobic by itself or can subsequently be hydrophobized by treatment with at least one surface-modifying substance. It is also possible for a particle which is hydrophobic per se to be additionally hydrophobized by treatment with at least one surface-modifying substance. Examples of surface-modifying substances include, but are not limited to, a hydrophobizing agent and a collector. Within the scope of the present invention, the term "hydrophobic" also includes that a "hydrophobized substance" such as a "hydrophobized magnetic particle" or a valuable matter containing material treated with a collector has a contact angle between water and the optionally hydrophobized surface of a particle against air of ≥90°.

In the scope of the present invention, "hydrophilic" means that a corresponding solid "hydrophilic particle" has a contact angle of water against air of <90°.

Methods for the acquisition of contact angles are known to the skilled artisan, for example by adding a drop of water on top of a thin layer of the powder and determining the angle at the liquid/solid interface with an CCD camera and software processing, see for examp Zisman, W. A. (1964). F. Fowkes, ed. Contact Angle, Wettability, and Adhesion. ACS. pp. 1-51.

EXAMPLES

Example 1

According to the Present Invention

As silicon comprising polymer, a solid methyl silicon resin (resin 1) of average composition [$CH_3SiO_{1.5}$]$_{-100}$ having a molecular weight Mw of 6600 g/mol is used.

2.06 g of resin 1 are dissolved in 150 ml of toluene. 150.31 g magnetite having a BET surface of 3 m$^2$/g, a $d_{10}$ of 2 μm, a $d_{50}$ of 4 μm and a $d_{90}$ of 9 μm, are added, and the black suspension is stirred at a temperature of about 70° C. for about one hour, Afterwards the pressure is decreased to 120 mbar at a temperature of 70° C. for 55 min, and then to 6 mbar at 70° C. and for 15 min. The solid that is obtained is dried, and a dry, grey solid is obtained. 152.35 g coated magnetite is obtained comprising 4.57 mg resin 1/m$^2$ of the surface of the magnetite particle.

Example 2

Comparative

As silicon comprising polymer, a solid ($CH_3$)$_3$Si(OR)/Si(OR)$_4$ cohydrolysate with a ratio of 0.67 and an amount of hydroxygroups of less than 0.3% (resin 2) is used. This polymer is a $SiO_2$-network that is terminated with ($CH_3$)$_3$Si-groups. This silicon comprising polymer has a molecular weight (weight average) of 6000 to 10000 g/mol.

2.04 g of resin 2 are dissolved in 150 ml of toluene. 150.03 g magnetite having a BET surface of 3 m$^2$/g, a $d_{10}$ of 2 μm, a $d_{50}$ of 4 μm and a $d_{90}$ of 9 μm, are added, and the black suspension is stirred at a temperature of about 70° C. for about one hour. Afterwards the pressure is decreased to 100 mbar at a temperature of 70° C. for 55 min, and then to 11 mbar at 70° C. and for 15 min. The solid that is obtained is dried, and a dry, grey solid is obtained. 152.14 g coated magnetite is obtained comprising 4.53 mg resin 1/m$^2$ of the surface of the magnetite particle.

Example 3

Comparison of core-shell particle according to example 1 according to the present invention and comparative core-shell particle according to example 2.

A naturally occurring sulfidic copper ore containing 0.62% by weight copper and 0.01% by weight molybdenum is treated with inventive core-shell-particles according to example 1 and comparative core-shell-particles according to example 2, separately.

The valuable-containing particles in the ore are selectively hydrophobised by potassium n-octyl xanthate and contacted with the core-shell-particles and magnetic agglomerates of the valuables present in the ore are obtained, whereas the gangue does not agglomerate. The magnetic agglomerates are then separated magnetically. The amount of separated agglomerates is then acquired by weighting (cycle I). The agglomerates are then separated using an aqueous solution of surfactant yielding an enriched copper concentrate. After second magnetic separation to separate the magnetic particles from the values, the magnetic particles are reused in a second ore treatment and the amount of magnetic agglomerates is acquired again (cycle II).

Results:

Use of core-shell-particles according to the present invention of example 1:

Cycle 1: 3.67 g concentrate

Cycle 2: 3.25 g concentrate, being 89% of cycle 1

Use of comparative core-shell-particles according to example 2:

Cycle 1: 3.18 g concentrate

Cycle 2: 1.04 g concentrate, being 33% of cycle 1

Whereas with core-shell-particles according to the present invention in cycle 2 still 89% of the amount of cycle 1 can be separated, with comparative core-shell-particles only 33% of agglomerates are obtained in cycle 2. These results clearly show that the shell according to the present invention is more stable under mechanical and chemical conditions of magnetic separation than the shell of the comparative particles.

The invention claimed is:

1. A process for separating at least one first material from a mixture comprising said at least one first material and at least one second material, wherein the process comprises the following steps:
   (A) contacting the mixture comprising the at least one first material and the at least one second material with at least one surface-modifying substance, optionally in the presence of at least one dispersant,
   (B) optionally, adding at least one other dispersant to the mixture obtained in step (A),
   treating the dispersion mixture from step (A) or (B) with at least one core-shell-particle wherein the core comprises:
   (i) at least one metal or a compound thereof, or
   (ii) a mixture of at least one metal or a compound thereof and at least one semimetal or a compound thereof,
   and the shell comprises at least one silicon comprising polymer comprising repeat units of the general formula (I)

—[SiR$^1$(OR$^2$)—O]—(I)

wherein
   R$^1$ is the same or different and is selected from hydrogen, linear or branched C$_1$-C$_{18}$-alkyl, unsubstituted or alkyl-substituted C$_5$-C$_{12}$-aryl, and
   R$^2$ is the same or different and is selected from hydrogen, linear or branched C$_1$-C$_{18}$-alkyl, unsubstituted or alkyl-substituted C$_5$-C$_{12}$-aryl, or —SiR$^1_x$(OR$^2$)$_{3-x}$, wherein x is 1 or 2 and R$^1$ and R$^2$ are the same or different and have the meanings as mentioned above,
   wherein the at least one metal or a compound thereof, or a mixture of at least one metal or a compound thereof and at least one semimetal or a compound thereof is magnetic, and the at least one first material to which the at least one surface-modifying substance is attached and the at least one core-shell-particle form an agglomerate, and
   (C) separating the agglomerate from step (C) from the mixture by application of a magnetic field.

2. The process according to claim 1 wherein after process step (D), (C) the process further comprises the following process step
   (D) cleaving the agglomerate which has been separated from the mixture in step (C) to obtain the at least one first material and the at least one core-shell-particle separately.

3. The process according to claim 2, wherein after cleavage according to step (D) the at least one magnetic core-shell particle is separated from a dispersion comprising said at least one magnetic core-shell-particle and said at least one first material by means of a permanent magnet or an electromagnet.

4. The process according to claim 2, wherein after step (D) the following step (E) is conducted:
   (E) further processing of particles or of the agglomerate from step (D) via smelting, extracting and/or wet chemical refining.

5. The process according to claim 1, wherein in process steps (A) and/or (B) a dispersant is present or added and the dispersion comprises from about 5 to about 40% by weight solid content wherein the solid content is based on a total amount of solids present.

6. The process according to claim 1, wherein after completion of process step (D), (E), or (F) (C) at least about 70% of the core-shell-particles are recovered from the process mixture.

7. The process according to claim 1, wherein the silicon comprising polymer further comprises repeat units of general formula (II)

—[SiR$^1_2$]—(II)

wherein
   R$^1$ is independently of another selected from hydrogen, linear or branched C$_1$—C$_{18}$-alkyl, unsubstituted or alkylsubstituted C$_5$-C$_{12}$-aryl.

8. The process according to claim 1, wherein the sum of the number of repeat units according to general formula (I), of repeat units according to general formula (II), if present, and the number of groups R$^2$ having the meaning —SiR$^1_x$(OR$^2$)$_{3-x}$, if present, is 10 to about 100,000.

9. The process according to claim 1, wherein the silicon comprising polymer comprising repeat unit of general formula (I) has a molecular weight Mw of about 500 to about 500000 g/mol (weight average).

10. The process according to claim 1, wherein the silicon comprising polymer is terminated with groups R$^1$ and/or groups —OR$^2$, wherein R$^2$ is independently of another selected from hydrogen, linear or branched C$_1$-C$_{18}$-alkyl or unsubstituted or alkylsubstituted C$_5$-C$_{12}$-aryl.

11. The process according to claim 1, wherein the at least metal or a compound thereof is selected from the group consisting of iron oxides, magnetic iron oxides and mixtures thereof.

* * * * *